US009829547B2

(12) United States Patent
Ziarati

(10) Patent No.: US 9,829,547 B2
(45) Date of Patent: Nov. 28, 2017

(54) HEAD-UP DISPLAY WITH EYE-TRACKER FOR MRI APPLICATIONS

(71) Applicant: Resonance Technology, Inc., Northridge, CA (US)

(72) Inventor: Mokhtar Ziarati, North Hollywood, CA (US)

(73) Assignee: Resonance Technology, Inc., Northridge, CA (US)

( * ) Notice: Subject to any disclaimer, the term of this patent is extended or adjusted under 35 U.S.C. 154(b) by 413 days.

(21) Appl. No.: 14/696,765

(22) Filed: Apr. 27, 2015

(65) Prior Publication Data

US 2015/0323617 A1    Nov. 12, 2015

Related U.S. Application Data

(60) Provisional application No. 61/990,629, filed on May 8, 2014.

(51) Int. Cl.
| | |
|---|---|
| *G01V 3/00* | (2006.01) |
| *G01R 33/28* | (2006.01) |
| *G06F 3/01* | (2006.01) |
| *G01R 33/42* | (2006.01) |
| *G01N 21/35* | (2014.01) |
| *G01R 33/48* | (2006.01) |

(52) U.S. Cl.
CPC ........... *G01R 33/283* (2013.01); *G01N 21/35* (2013.01); *G01R 33/42* (2013.01); *G06F 3/013* (2013.01); *G01R 33/4806* (2013.01)

(58) Field of Classification Search
USPC ......................................................... 324/318
See application file for complete search history.

(56) References Cited

U.S. PATENT DOCUMENTS 4,901,141 A    2/1990 Costello
5,076,275 A *  12/1991 Bechor .................. A61B 5/055
                                                    324/318
(Continued)

OTHER PUBLICATIONS

Semiconductor Components Industries, LLC, NOIV1SN2000A, VITA 2000 2.3 Megapixel 92 FPS Global Shutter CMOS Image Sensor, Jul. 2012, Rev. 4, NOIV1SN2000A/D.

*Primary Examiner* — Rodney Fuller
(74) *Attorney, Agent, or Firm* — Larry K. Roberts

(57) ABSTRACT

A head-up display and eye-tracker system, suitable for use with a patient in an MRI tube during an MRI procedure. An electronic display assembly includes an outer display tube housing for housing an electronic display device for generating images, the outer tube housing fabricated of an electrically conductive, non-ferrous material. An eye-tracker camera assembly includes an outer camera tube housing for housing an electronic camera sensor, the outer tube camera housing fabricated of an electrically conductive, non-ferrous material. An eyepiece assembly includes an outer housing. A beam splitter assembly includes a beam splitter block having a receptacle holding a beam splitter, the block formed of an electrically conductive, non-ferrous material. The beam splitter reflects light from the display onto the patient's eye, and allows light reflected from the patient's eye to pass to the camera sensor. In another embodiment as a display system, the eye-tracker camera assembly is omitted.

34 Claims, 20 Drawing Sheets

(56) References Cited

U.S. PATENT DOCUMENTS

| | | | | |
|---|---|---|---|---|
| 5,339,813 | A | * | 8/1994 | DeYoe ................. A61B 5/0555 359/419 |
| 5,345,281 | A | * | 9/1994 | Taboada ................. A61B 3/113 351/209 |
| 5,412,419 | A | * | 5/1995 | Ziarati ................. G01R 33/283 324/318 |
| 5,706,070 | A | * | 1/1998 | Reich ................. G01R 33/283 348/E13.041 |
| 5,877,732 | A | * | 3/1999 | Ziarati ................. G01R 33/283 345/8 |
| 6,847,336 | B1 | | 1/2005 | Lemelson et al. |
| 6,873,714 | B2 | | 3/2005 | Witt et al. |
| 6,926,429 | B2 | | 8/2005 | Barlow et al. |
| 7,526,330 | B1 | * | 4/2009 | Randell ................. A61B 5/055 324/309 |
| 8,477,425 | B2 | | 7/2013 | Border et al. |
| 8,554,304 | B2 | * | 10/2013 | Vangdal ................. A61B 5/055 345/81 |
| 8,866,480 | B2 | | 10/2014 | Waffenschmidt et al. |
| 9,039,632 | B2 | * | 5/2015 | Kiderman ................. A61B 5/16 600/558 |
| 2005/0283068 | A1 | | 12/2005 | Zuccolotto et al. |
| 2009/0093705 | A1 | * | 4/2009 | Vangdal ............... G01R 33/283 600/410 |
| 2010/0238161 | A1 | | 9/2010 | Varga et al. |
| 2013/0207887 | A1 | * | 8/2013 | Raffle .................... G02B 27/00 345/156 |
| 2014/0002587 | A1 | | 1/2014 | Aguren |
| 2014/0022283 | A1 | | 1/2014 | Chan et al. |
| 2014/0192326 | A1 | * | 7/2014 | Kiderman ................. A61B 5/16 351/210 |
| 2016/0223819 | A1 | * | 8/2016 | Liu .................... G02B 27/0172 |

\* cited by examiner

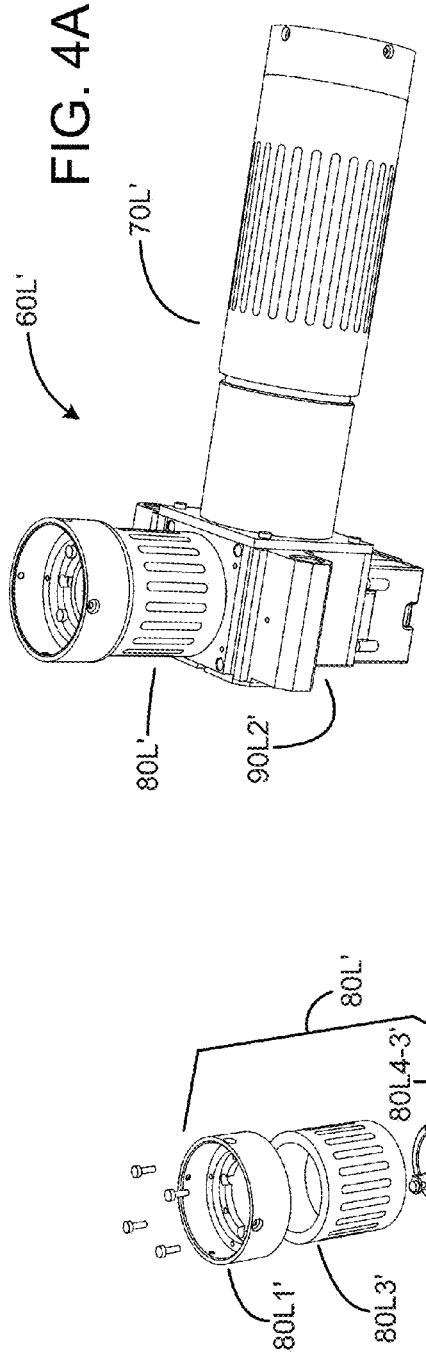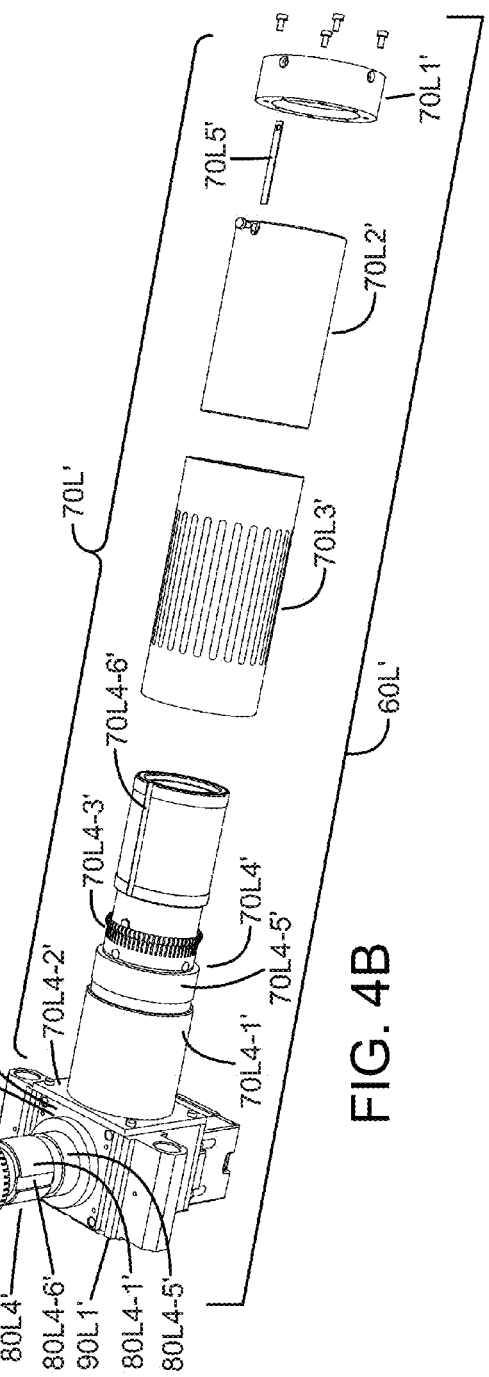

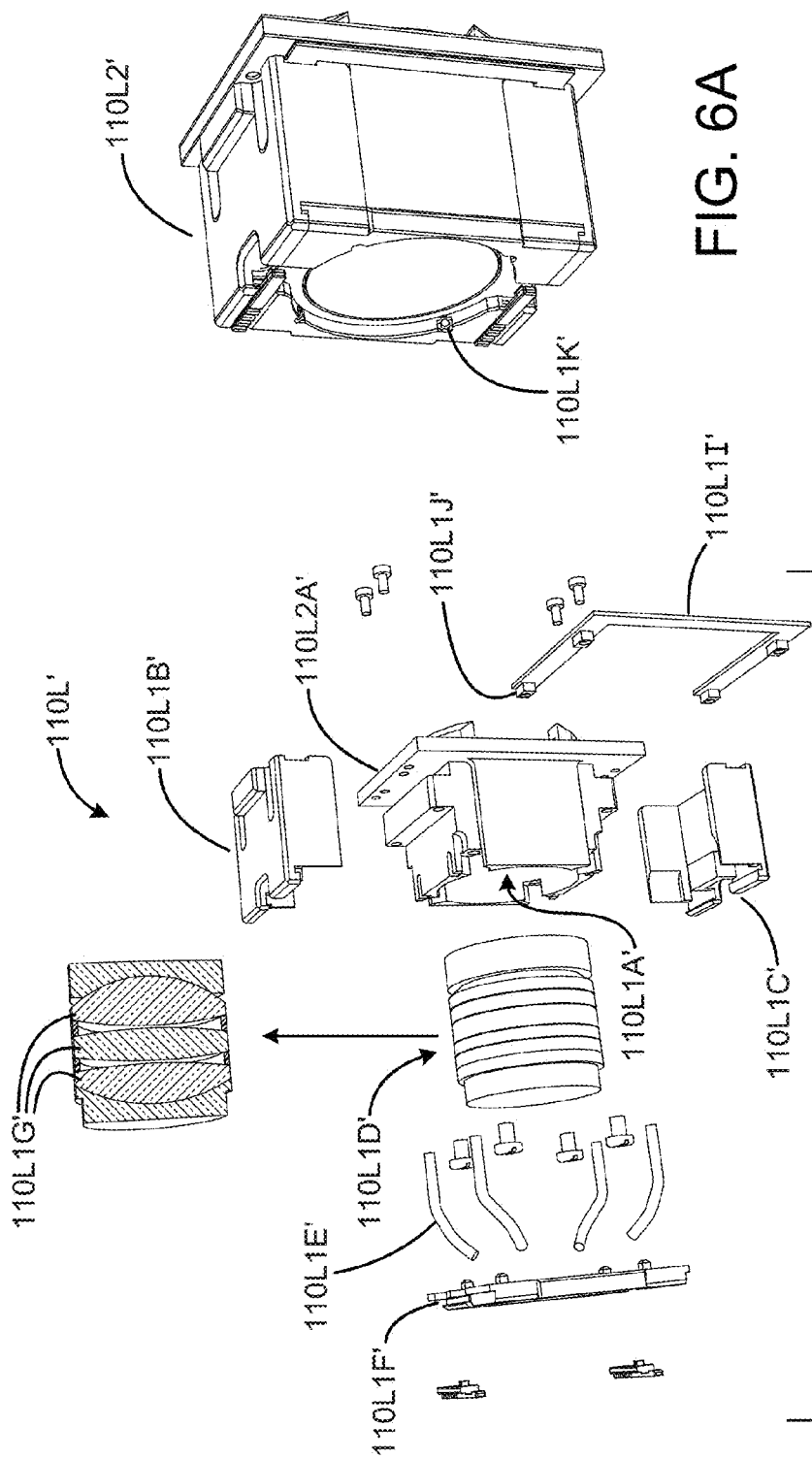

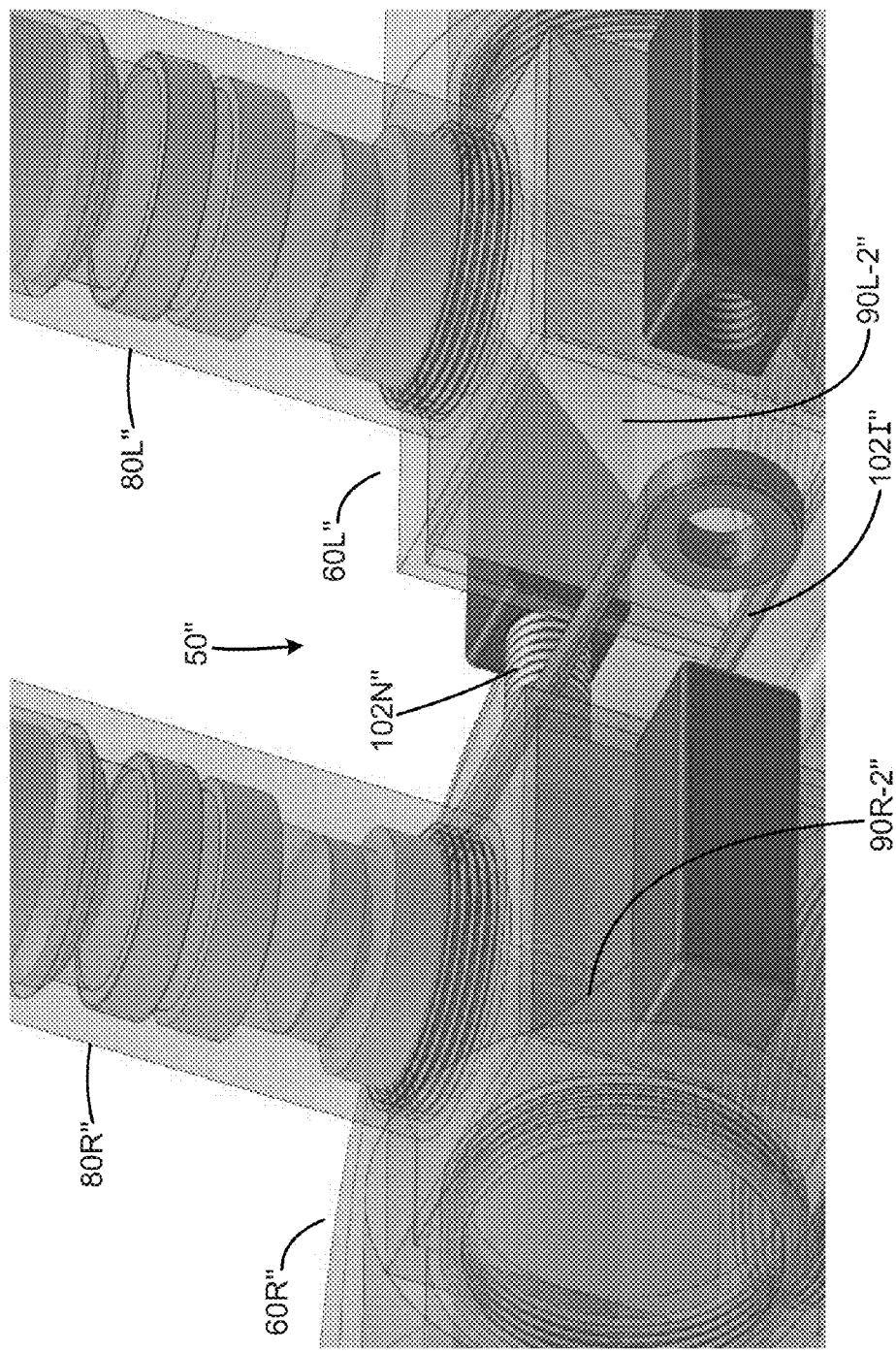

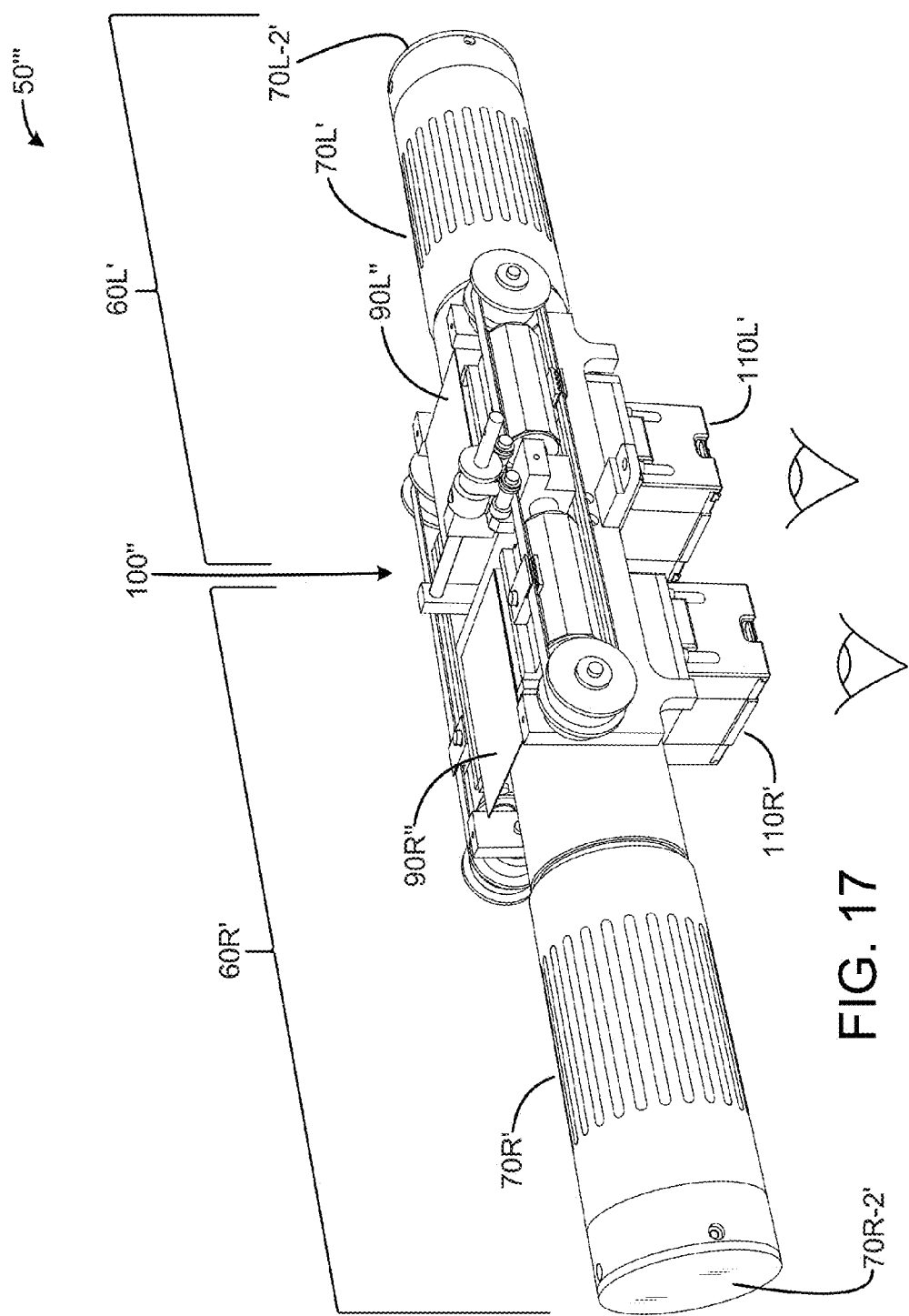

HEAD-UP DISPLAY WITH EYE-TRACKER FOR MRI APPLICATIONS

CROSS-REFERENCE TO RELATED APPLICATION

This application claims the benefit of U.S. Provisional Application No. 61/990,629 filed May 8, 2014, the entire contents of which are hereby incorporated by reference.

BACKGROUND

The use of displays in a Magnetic Resonance Imaging (MRI) equipment environment was first developed in the late 80's and early 90's, as described in U.S. Pat. Nos. 5,412,419, 5,432,544, 5,627,902, and 5,877,732.

MRI is one of the fastest changing imaging modalities in the world. In addition to the use of MRI for the diagnostic purpose, other applications such as functional MRI (fMRI) have been a major use of this imaging modality. The fMRI field requires various stimulation tasks such as an auditory and visual delivery system along with eye tracking to record the movements of the eyes during the procedure.

The current technology for displaying visual stimuli and recording the eye movement in functional MRI applications has many limitations due to the constraint of the strong magnetic field and high-energy radio frequency signals.

In both the goggle display type and the visor display type, the current technology uses very fine mesh in front of the actual display to block the emission of the RF to the outside and cause interference to the MRI signal. The mesh will create some disturbance to the visual effect of the display for the subject undergoing the functional MRI.

Eye-trackers in most cases are video-based, meaning there is a camera located outside of the bore of the MRI magnet, or in some designs a coherent fiber optic bundle used, similar to the devices used for endoscopy, to look at the eye. This technology also poses a problem for the researchers, because the set up time is very long and the center of the eye with respect to the camera has to be fixed. A slight movement of the subject's head will throw off the calibration of the eye tracker. The eye is looking to a display for presenting stimuli to the subject and the eye tracker camera has to look to the corner of the eye to observe the eye from under the eye LED.

Currently, most facilities use a video projector or LCD display located on the back of the magnet and the subject has to look into a reflective mirror to view the images. This make the tracking of the eye at the same time more difficult. Because the subject has to be able to look at the video projected to him/her either through the reflected mirror or via the optical lens, the path of the camera looking at the center of the eye will be blocked; therefore the MRI operator has to fix the camera to look at the eye with an angle not perpendicular to the eye. This causes the eye tracker to lose track as the eye moves farther away from the center.

BRIEF DESCRIPTION OF THE DRAWINGS

Features and advantages of the disclosure will readily be appreciated by persons skilled in the art from the following detailed description when read in conjunction with the drawing wherein:

FIG. 4A is an isometric view of a camera, eyepiece and display assembly for one eye, of the system of FIG. 2. FIG. 4B is a partially exploded view of the assembly of FIG. 4A.

FIG. 6A is an isometric view on one of the eyepiece assemblies of the system of FIG. 2. FIG. 6B is an exploded view of the eyepiece assembly of FIG. 6A.

FIG. 10 illustrates in isometric view features of the embodiment of FIGS. 9A-9C.

FIGS. 9A-9C.

FIG. 17 illustrates a further embodiment, showing a display system as in FIG. 2, but without the eye-tracker camera elements.

DETAILED DESCRIPTION

Figure 1:
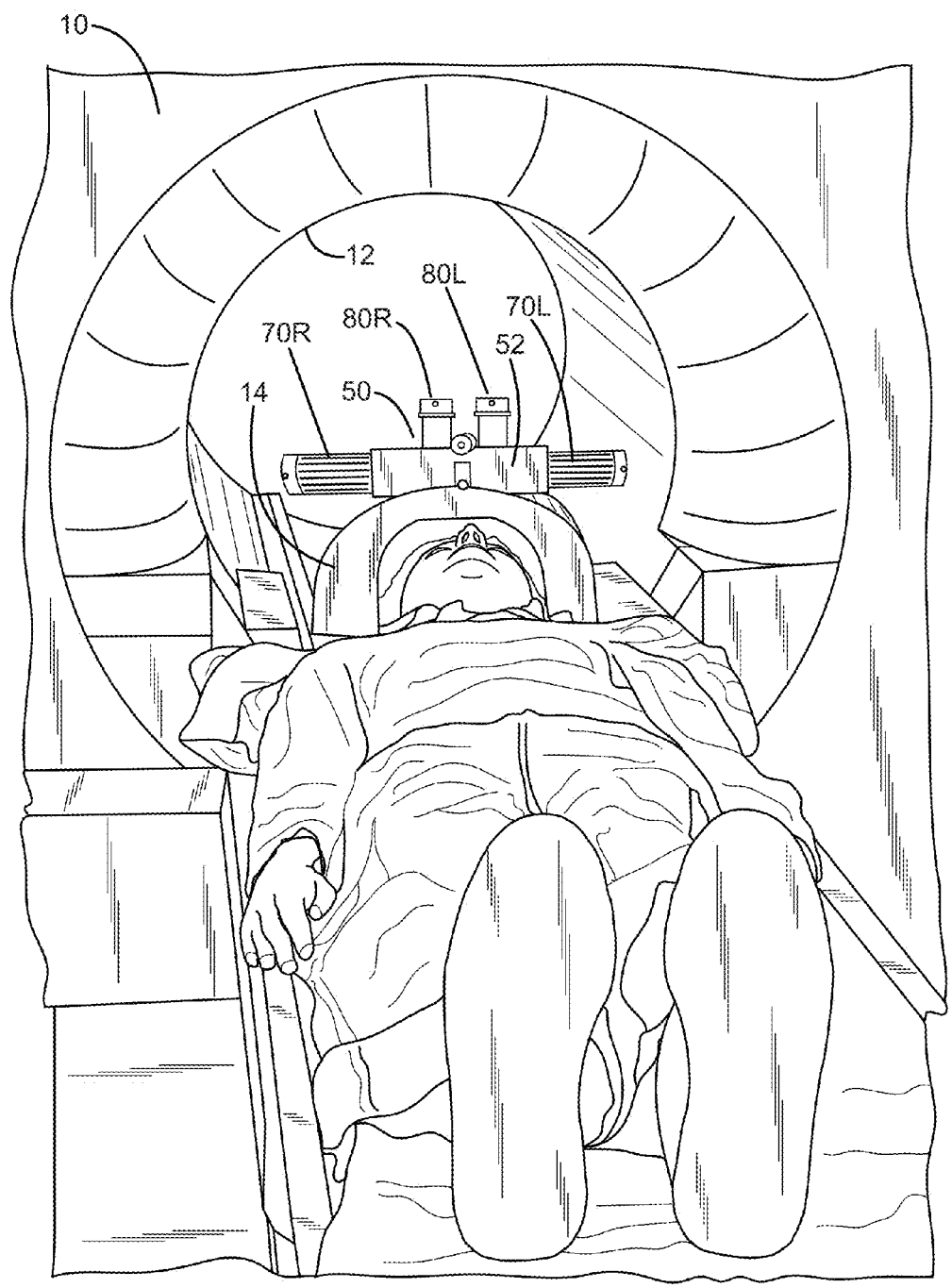
FIG. 1 is a diagrammatic isometric view, illustrating a patient in an MRI tube, and a head coil mounting an exemplary embodiment of a heads-up display and eye-tracker system.

In the following detailed description and in the several figures of the drawing, like elements are identified with like reference numerals. The figures are not to scale, and relative feature sizes may be exaggerated for illustrative purposes.

Exemplary embodiments of a new heads-up display and eye-tracker system are described, with particular utility for MRI applications. In accordance with aspects of the invention, one embodiment of the system includes a relay optics housing for the display used as a waveguide to block the emission of the RF to the outside and cause interference to the MRI signal, and eliminate the need for a mesh shield over the actual display, in the optical path between the display and the user's eye. A similar technique may be used with the camera sensor section.

In accordance with a further aspect, the use of a beam splitter enables the system to provide an excellent image of the eye at all times while the observer is looking into the eyepiece and seeing the actual display. This provides a robust eye tracker signal for the system users and researchers, saves set-up time and minimizes repeat scans while getting accurate data.

In an exemplary embodiment, the display optics are designed to have 50 degree FOV (field of view). In the normal setting (FIG. 16A), both eyes look into the display screen with 100% overlap. This means the virtual image for the right and the left eye are totally super imposed on top of each other. The observer, the patient in the MRI tube, sees 50 degree FOV at normal setting.

In many cases, the researcher has a need to send visual stimuli to the peripheral view of the patient's eyesight and there is a need for a wider FOV. In an alternate embodiment of the heads-up display and eye-tracker system, the display optic can be tilted to provide less overlap of the respective left and right images, e.g. to provide 80% overlap in one example (see FIG. 16B), to provide a FOV of 58 degrees, or even further to have, for example, 20% over lap (FIG. 16C), and hence increase the FOV to approximately 80 degrees.

Significant features of exemplary embodiments of the invention include one or more of the following:

A. High-resolution displays without the need of any shielding between the display and the eye piece, to deliver clearer images to the subject, e.g. during fMRI tasks in the display view path. In an exemplary embodiment, the displays are OLED (organic light emitting diode) displays.

B. New concept of the eye tracking camera to see the cornea continuously while the subject is looking into the eyepiece.

C. Variable FOV to enable the researcher to stimulate the peripheral vision.

D. A faster eye tracker camera, for example 1000 Hz, can be employed, since the optics may be larger than conventional systems and allow light to the sensor for a high speed camera. The optics in the system may be supported outside the head coil, allowing more room to design larger lenses.

E. By having such relay optics, and with the availability of higher resolution OLED displays, an exemplary embodiment of the display can provide 1920×1200 pixel resolution.

F. Ease of assembly and reproducibility, in embodiment utilizing a waveguide-like shielding.

The following formula and table show the relation between the image overlap and the FOV.

Formula: $\theta = \arctan[(2-p)(\tan 25°)]$

Where p is the overlap percentage, and FOV=$2\theta$

| Overlap | FOV | Comments |
|---------|------|----------|
| 100% | 50.0 | Full binocular view |
| 90% | 54.3 | |
| 80% | 58.5 | |
| 70% | 62.4 | |
| 60% | 66.3 | |
| 50% | 69.9 | |
| 40% | 73.5 | |
| 30% | 76.8 | |
| 20% | 80.0 | |
| 10% | 83.1 | |
| 0% | 86.0 | No binocular field |

Figure 1A:
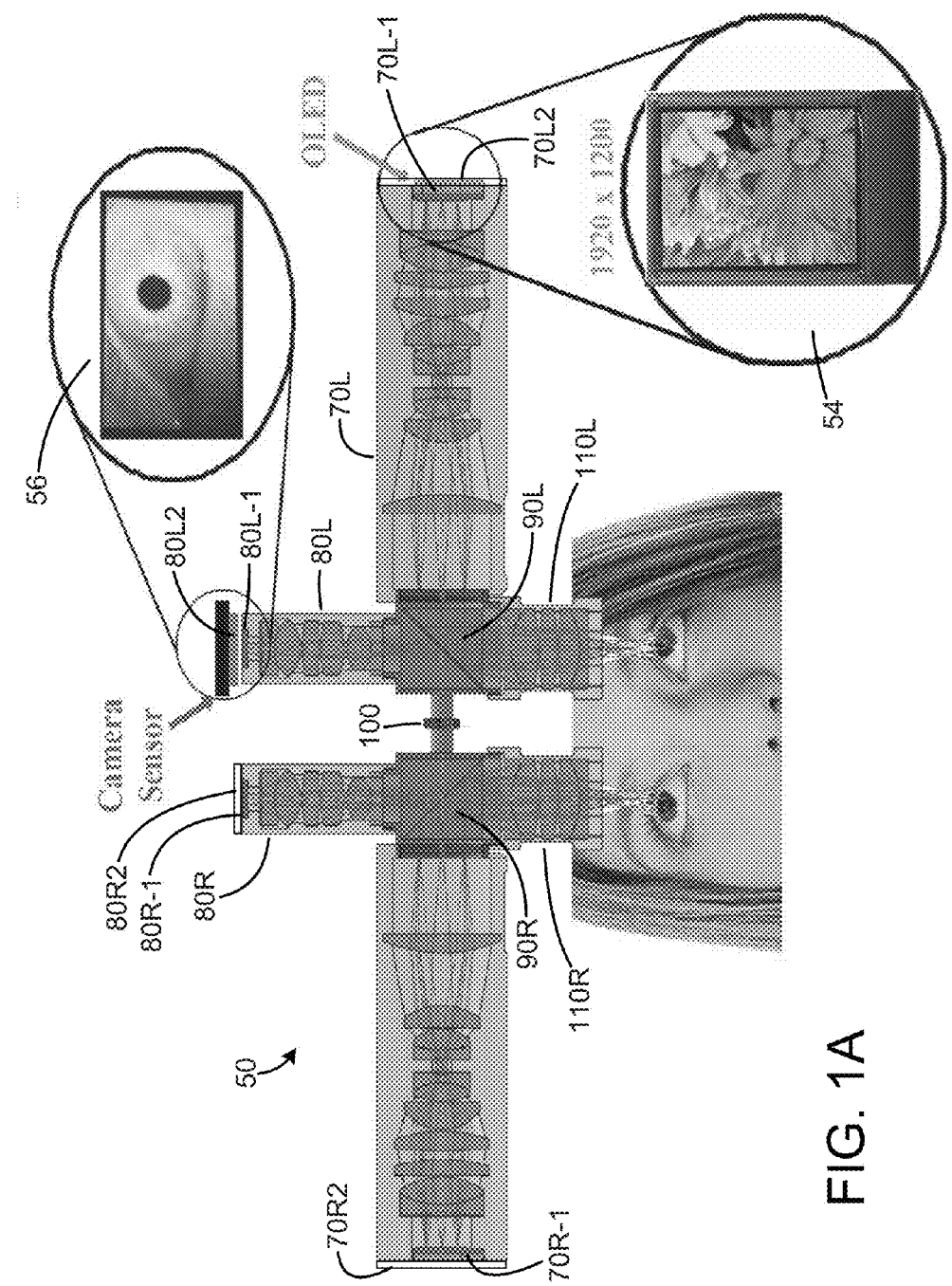
FIG. 1A is a diagrammatic illustration of the system, showing the patient's eyes and features of the system.

FIGS. 1 and 1A show an exemplary application for an exemplary embodiment of a heads-up display and eye-tracker system 50, showing a patient positioned for a procedure in the tube 12 of an MRI system 10, with an MRI head coil 14 positioned in the tube with the patient's head within the head coil. The head coil 14 supports the system 50 above the patient's eyes, so that the eye-trackers have an unobstructed view of the patient's eyes.

The system 50 includes a housing 52, left and right displays 70L and 70R for generating images for viewing by the patient, left and right eye trackers 80L and 80R, and left and right eye pieces 110L, 110R. Beam splitter assemblies 90L and 90R for the left and right eyes respectively function to reflect visible image light from the displays onto the patient's eyes, while allowing the cameras to receive eye tracking infrared energy reflected from the patient's eyes. FIG. 1A depicts light rays through the optics between the patient's eyes on the one hand, and the respective cameras, beam splitters and eyepieces, and the eye-tracker cameras, optics, beam splitters and eyepiece optics.

The housing tubes for the displays in an exemplary embodiment are fabricated of an electrically conductive, non-ferrous material such as brass or aluminum, and form waveguides for the image light. The length of the tubes is selected to be sufficiently long in relation to the inner diameter of the tubes so as to effectively prevent image radiation from affecting the MRI images. Typically the length is at least about three times the inner diameter of the tube, for example, a six inch tube length, and an internal diameter of 2 inches. As a result, no mesh shielding is utilized for the embodiment shown in FIGS. 1 and 1A. The distal tube ends are closed with an electrically conductive, non-ferrous cover plate 70L-2 and 70R-2 (FIG. 1A), such as brass or aluminum. In another embodiment, the tubes may be fabricated of a plastic material plated with an electrically conductive, non-ferrous coating. In a further embodiment, the tubes for the display and camera assemblies may be fabricated of a plastic, non-conductive material. In this further embodiment, the display generators and the camera sensors may be shielded with very fine conductive wire mesh, made of a non-ferrous material, to prevent radiation from these elements from affecting the MRI images.

Thus, the system includes an RF shielding system configured to block the emission of RF energy emitted by the display generators and camera sensors to the outside and cause interference to the MRI signals, thereby shielding the display and camera systems from affecting the MRI images. A preferable RF shielding system is to employ tubes for the display and sensor assemblies which are fabricated of an electrically conductive, non-ferrous material as described above. Another RF shielding system employs the fine mesh shielding system covering the display generators and the camera sensors, and in that case, the tubes may be fabricated of non-conductive material. The later shielding system has the disadvantage of the mesh degrading the image quality, but may be acceptable in some applications.

Figure 15:
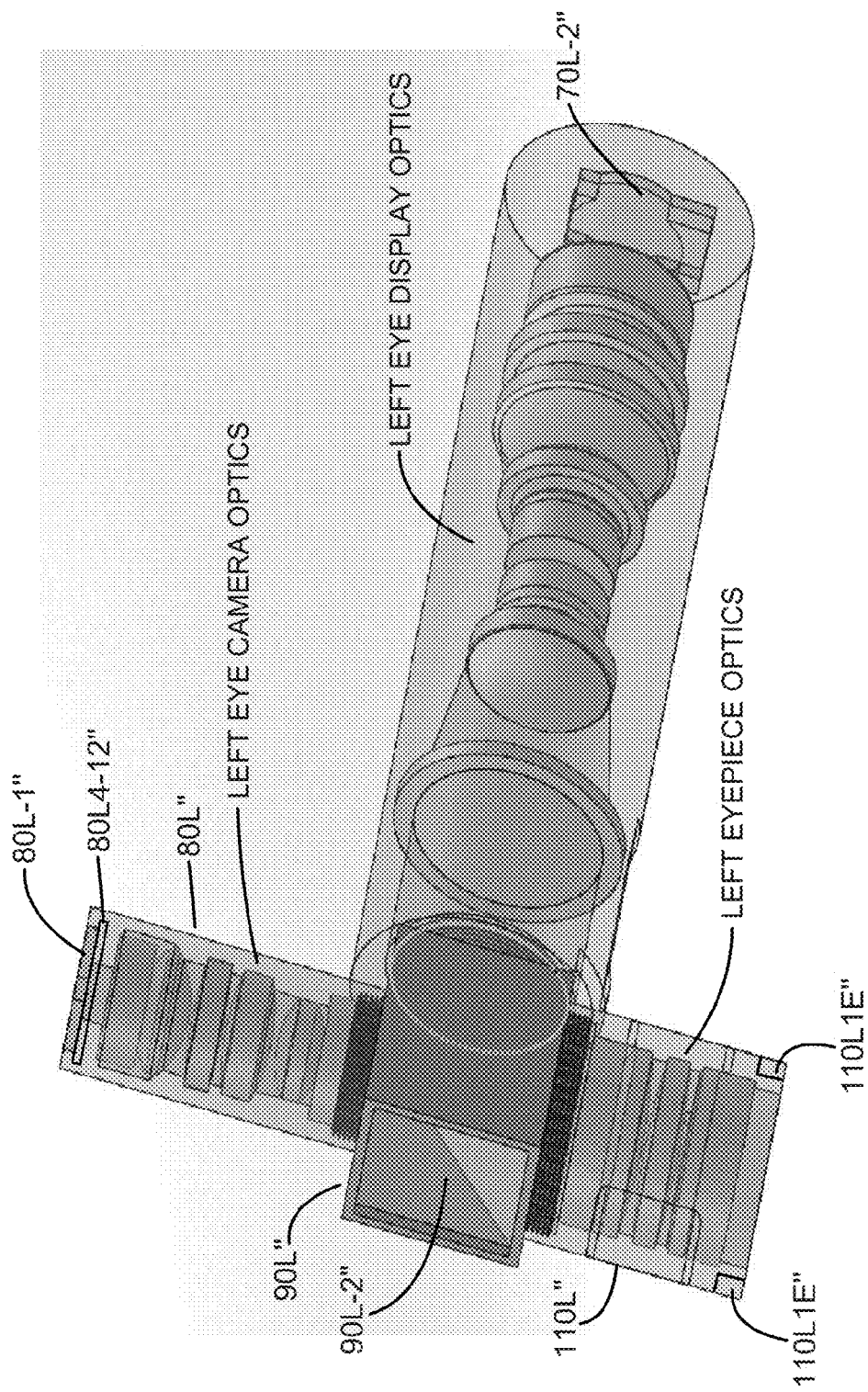
FIG. 15 is an isometric diagrammatic illustration of one eye display and eye tracker, for the system of FIG.

Each display includes a display device 70L-1, 70R-1, which may be an OLED display with high resolution, e.g. 1920 by 1200 pixel resolution, to generate an image such as image 54 (FIG. 1A). The image is passed through display optics to the corresponding beam splitter 90L, 90R, where the image is reflected onto the patient's eye. The eye-trackers include a camera sensor 80L-1 and 80R-1 which are sensitive to infrared energy. Sensors suitable for the use are commercially available, e.g. including CMOS CCD sensor arrays. One exemplary sensor is the VITA 2000 2.3 Mega-pixel image sensor, marketed by ON Semiconductor. Infrared (IR) LEDs or fiber optic emitters emit IR onto the patient's eyes, which is reflected from the eyes and passed through eye-tracker optics to the camera sensors, to produce images of the eye, such as image 56 (FIG. 1B). Filters (e.g. filter 80L4-12", FIG. 15) are placed in the optical path before the camera to allow only IR energy to pass through to the camera sensors. Eye-tracker tube end covers 80R-1, 80R-2 are attached at the open ends of the respective tubes, and are fabricated of an electrically conductive, non-ferrous material, such as brass or aluminum, to block noise and RF energy from escaping the tube and affecting the MRI images.

The system 50 includes a mechanism 100 which allows adjustment of the system for the inter-pupil distance (IPD) of the patient, and optionally the angular orientation of the left and right eye camera and display systems, to adjust the field of view (FOV) of the system. The system optionally includes focus adjustments for the optics for the displays and eye-trackers.

The heads-up display and eye-tracker system 50 also includes wiring, preferably non-ferrous, to carry power and signals to the cameras and the displays. The system may be controlled by a controller in the MRI control room. Exemplary MRI installations and control rooms are described in pending applications 13725339, filed Dec. 21, 2012, entitled MRI-compatible 3D Television and Display System; and 14142414, filed Dec. 27, 2013, entitled Universal Interface System for MRI Applications, the entire contents of which applications are incorporated herein by this reference. The controller provides the image signals for the displays, and receives the eye tracker images for review and processing. The power and signal wiring cables are attached to connectors built into the end covers for the display and the camera tube assemblies. The connectors are electrically connected to circuit boards mounting the cameras and displays.

The left and right eye displays can be controlled to display the same image to each eye, or to present different images to each eye, for example stereoscopic images, which can present three-dimensional images. An example of different images is a red image presented to one eye, while a green image is presented to the other eye. The system may be a binocular system, with components for the left eye and the right eye. For some applications, the system might include only the components for one eye or the other, i.e. a monocular system. For other applications, the system may be a binocular system, with images presented to only one eye at a time.

FIGS. 2-8B illustrate features of an exemplary embodiment of a heads-up display and eye-tracker system 50'. The elements corresponding to the elements of system 50 (FIGS. 1, 1A) are identified with the same number and a prime.

Figure 2:
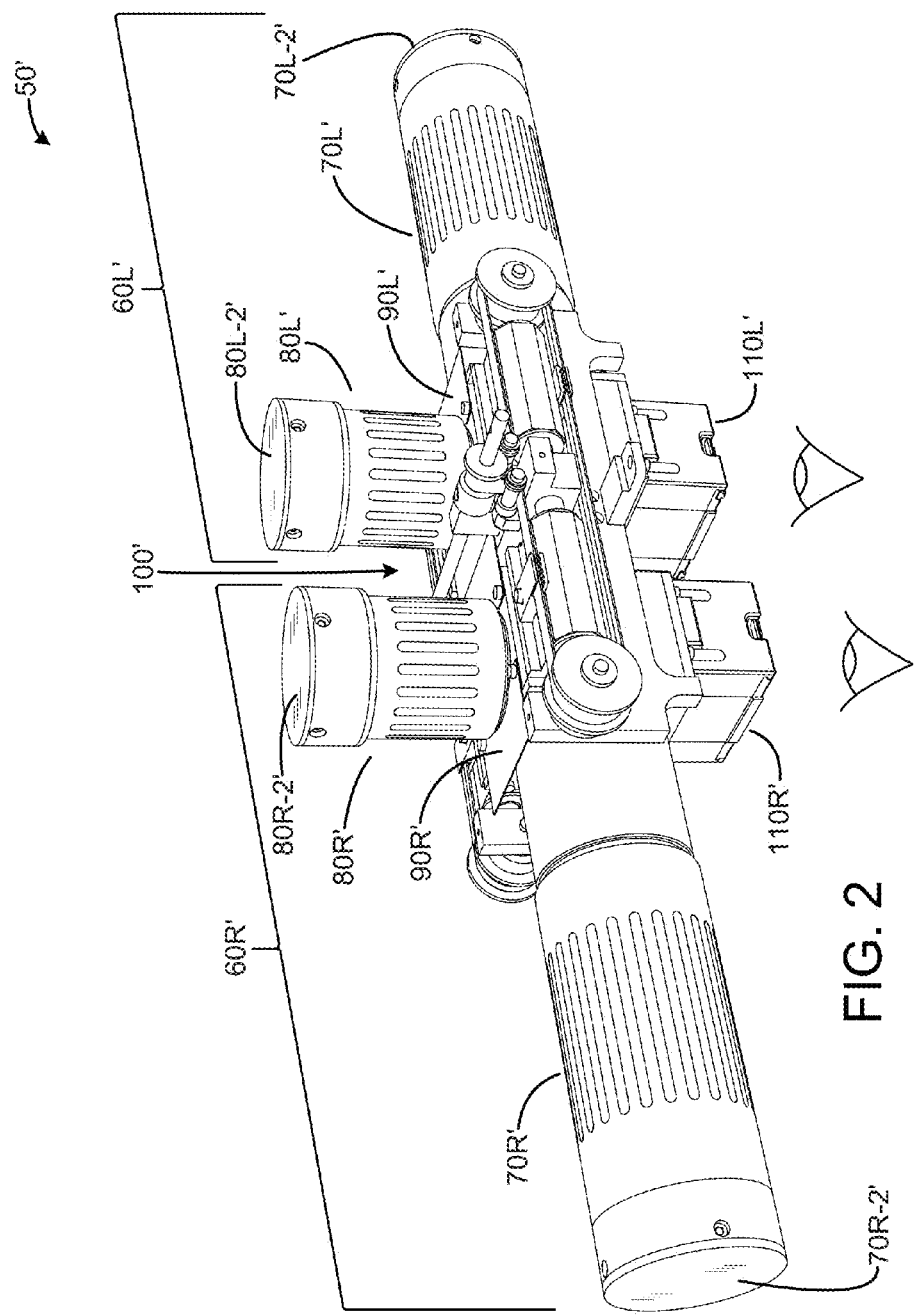
FIG. 2 is an isometric view of an exemplary embodiment of a heads-up display and eye-tracker system for use in the environment illustrated in FIG. 1, in which an outer cover is omitted for clarity.
Figure 2A:
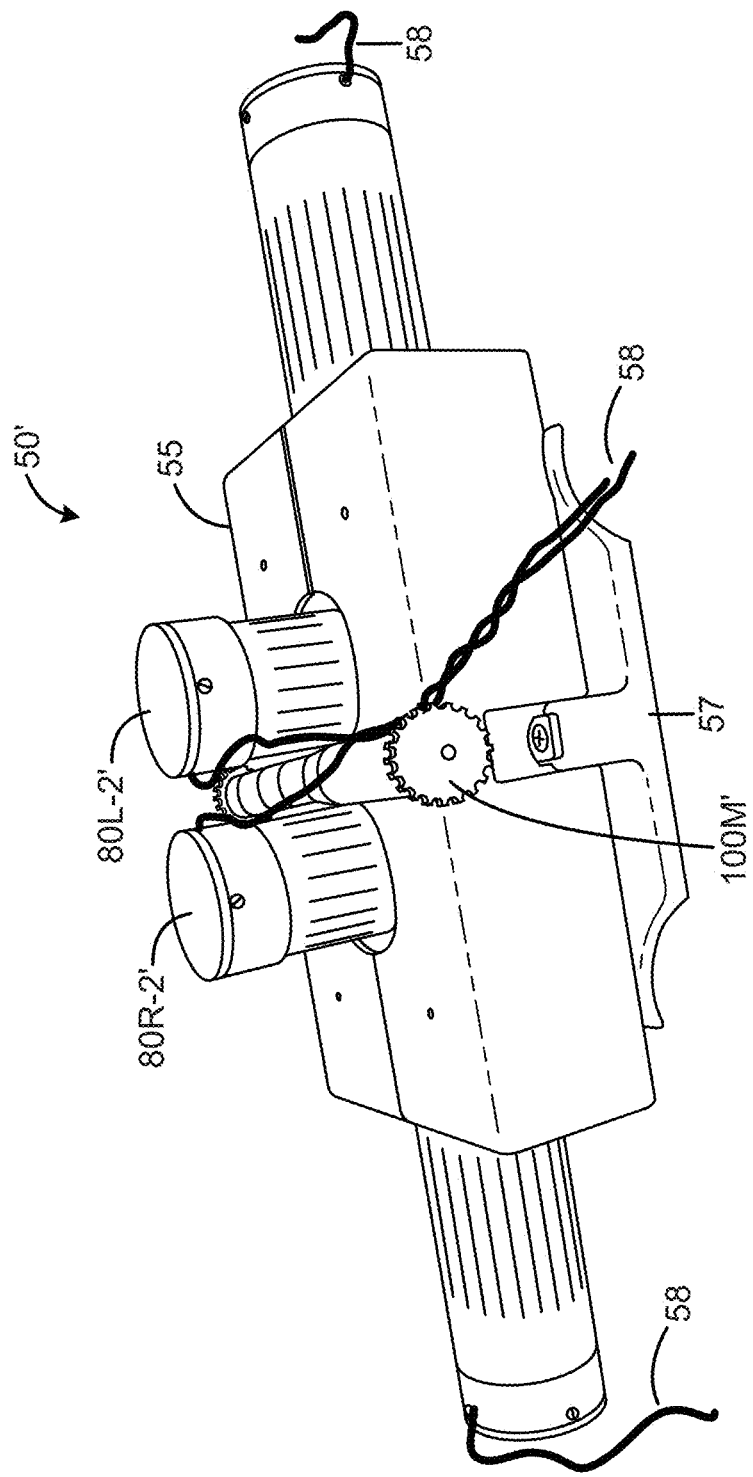
FIG. 2A illustrated an isometric view of the system of FIG. 2, showing the cover.

FIG. 2 shows the system 50' in isometric view, with the respective camera (80L', 80R'), display (70L', 70R'), beam splitter (90L', 90R') and eye piece (110L', 110R') assemblies for the respective eyes indicated as 60L' and 60R'. The assemblies 60L' and 60R' are joined together by a mechanism 100' allowing adjustment of the system for the inter-pupil distance (IPD) of the patient. End covers 70R-2', 80L-2', 80R-2' are visible in FIG. 2. FIG. 2A shows an isometric view of the system 50', with cover 56 formed of an electrically conductive non-ferrous material, with signal and power cabling 58 for the respective displays and cameras. Covers 80L-2' and 80R-2' are also visible. Knobs 100M' are mounted on shaft 102F' of the IPD mechanism 100. A yoke or base 57 is fitted to the housing 55, to support the system 50' on the head coil 14 (FIG. 1).

Figure 3:
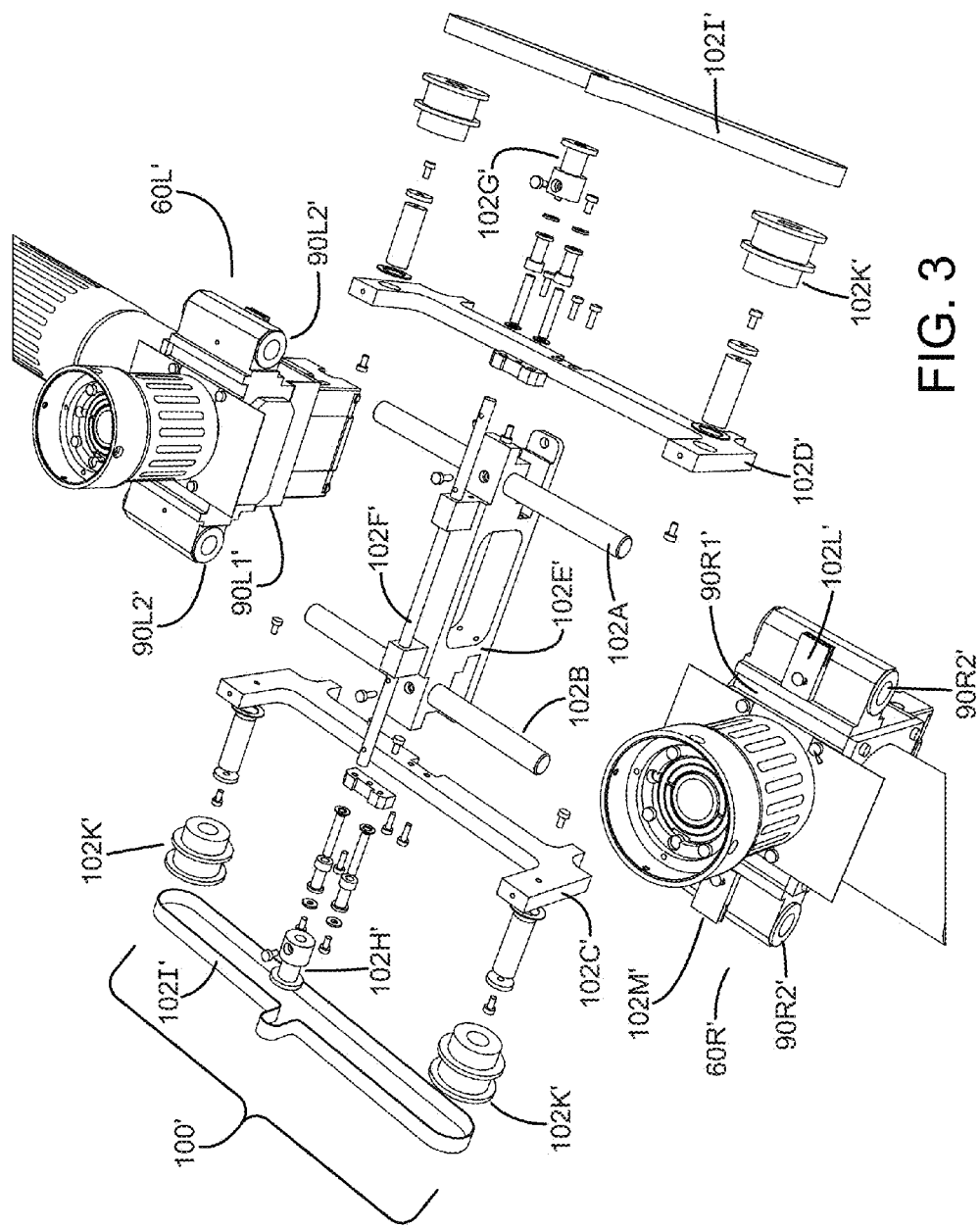
FIG. 3 is an exploded isometric view of an exemplary embodiment of a system for adjusting the inter-pupillary distance (IPD) between the eye pieces of the system of FIG. 2.

FIG. 3 is an isometric view, showing an exemplary embodiment of the mechanism 100'. The mechanism includes a pair of shafts 102A', 102B' whose ends are positioned within shaft sleeves 90L2' and 90R2' of respective beam splitter blocks 90L1' and 90R2', so that assemblies 60L' and 60R' can be moved toward each other or spaced further apart along the axes of the shafts. IPD rails 102C' and 102D' are attached to opposed ends of a center plate 102E'. An IPD shaft mounts belt drive pulleys 102G'1 and 102 H', which engage respective belts 102I' and 102J' mounted on opposed pairs of pulleys 102K' to ends of the respective rails. Belt clamps 102L' and 102M' are mounted to beam splitter block 90R1', and fix the positions of the belts relative to the beam splitter block 9R1'. As the IPD shaft 102F' is rotated, the belts will pull or push the left assembly 60L' toward or away from the right assembly 60R', thereby adjusting the system for different IPDs of patients.

Figure 5A:
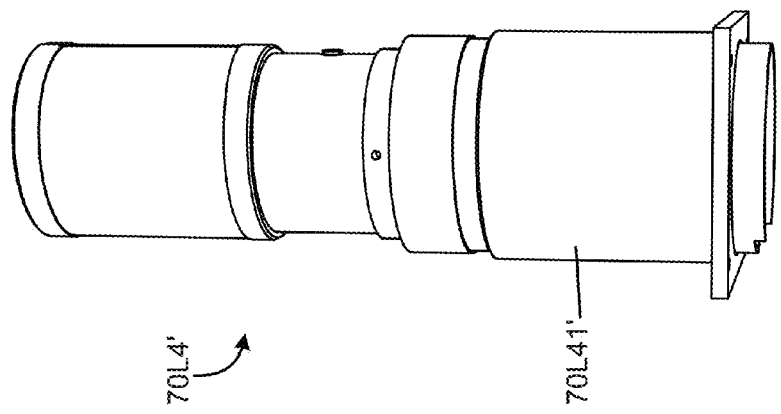
FIG. 5A shows one of the display tube assemblies in isometric view, of the system of FIG. 2.
Figure 5B:
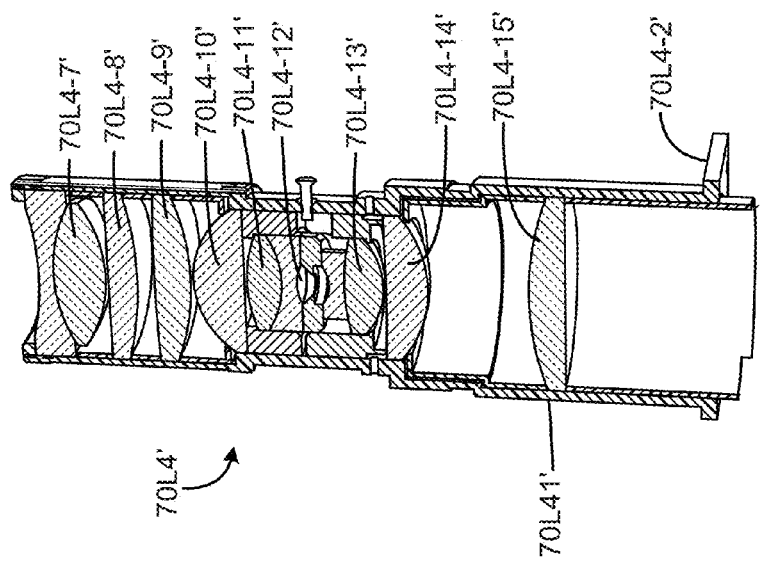
FIG. 5B is a simplified cross-sectional view of the tube assembly of FIG. 5A.

FIGS. 4A-4B illustrate one exemplary assembly 60L', with assembly 60R' being structurally similar. Beam splitter block 90L1 is attached to display assembly 70L' and to eye tracker camera assembly 80L'. In this exemplary embodiment, the assemblies 60L' and 60R' include focus mechanisms, to move the display and eye tracker camera in relation to the display optics and the camera optics, respectively. The display assembly 70L' includes a display tube assembly 70L4' with optical elements, a display focus barrel 70L3', a display focus tube 70L2', and a display holder 70L1' which mounts the display device. FIGS. 5A and 5B show an exemplary embodiment of the display tube assembly 70L4'.

The display tube assembly includes an outer housing 70L4-1' fabricated of an electrically conductive, non-ferrous material such as brass or aluminum, with a flange 70L4-2' configured for attachment to the beam splitter block 90L1' by non-ferrous threaded fasteners. The length of the tube plus the length of the beam splitter block is at least three times the inner diameter of the tube, to provide shielding of RF energy from leaking from the display and into the MRI magnet room. An RF gasket 70L4-3', such as a beryllium copper RF gasket, is fitted around a periphery of the tube housing. Outer surface 70L4-5' is threaded, to engage corresponding internal threads at the end of the display focus barrel 70L3'. Display focus tube 70L2' fits within the end of the focus barrel 70L3' distal from the display tube assembly, and has the display holder 70L1' mounted to its outer end. Both the focus tube and display holder are fabricated of an electrically conductive non-ferrous material such as brass or aluminum. The inner end of the focus tube engages the RF gasket 70L4-3' when assembled. The threads on the focus barrel and surface 70L4-5' are fine threads, and the focus barrel when rotated serves to move the focus tube and display holder toward or away from the beam splitter block, within a travel range of 1 mm or so in this exemplary embodiment, allowing some focus control of the image. A display focus key or pin 70L5' is secured at the inside of the focus tube 70L2' and engages channel 70L4-6' to prevent rotation of the display holder 70L1' as the focus barrel is turned.

The display tube assembly 70L4' mounts the optics which provide the optical path of the image light to the beam splitter. The optics include lenses 70L4-7'-70L4-11' and 70L413'-70L4-15', and define a field stop at 70L4-12' (FIG. 5B). Spacer elements hold the lenses in the appropriate positions within the tube.

Referring again to FIGS. 4A and 4B, camera tube assembly 80L' is mounted to the beam splitter block 90L1', in a transverse orientation relative to the display tube assembly 70L'. Assembly 80L' includes camera housing 80L1' for mounting the eye-tracker camera, camera focus barrel 80L3', camera focus tube 80L2', and camera display tube assembly 80L4'. The focus barrel has internal threads which engage threads on surface 80L4-5'. The assembly elements are assembled together in a similar way as described above regarding the display assembly 70L' to provide a mechanism to move the camera through a range of movement, typically 1 mm, toward and away from the beam splitter block 90L1'. A camera key 80L5' is attached to the focus tube and engages channel 80L4-6' on the camera tube housing 80L4-1', preventing rotation of the camera housing as the camera focus barrel is rotated.

Figure 7A:
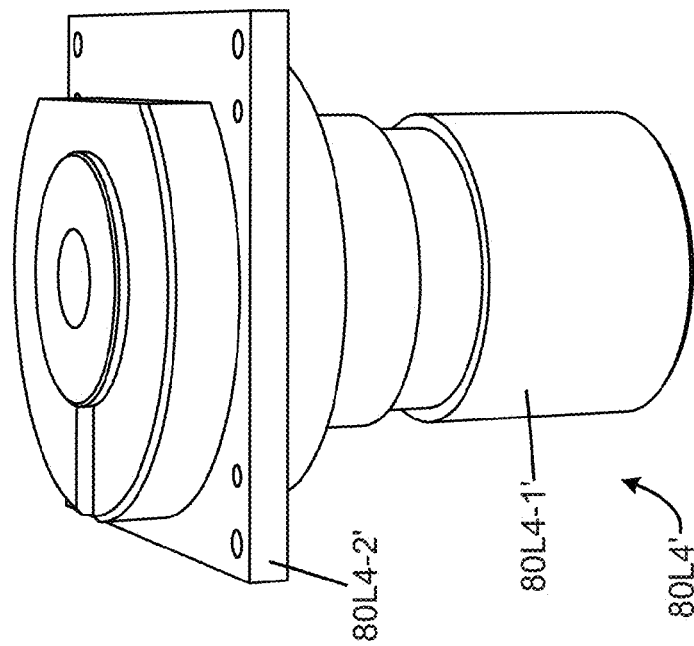
FIG. 7A is an isometric view of one of the cameral optics assemblies for the system of FIG. 2.
Figure 7B:
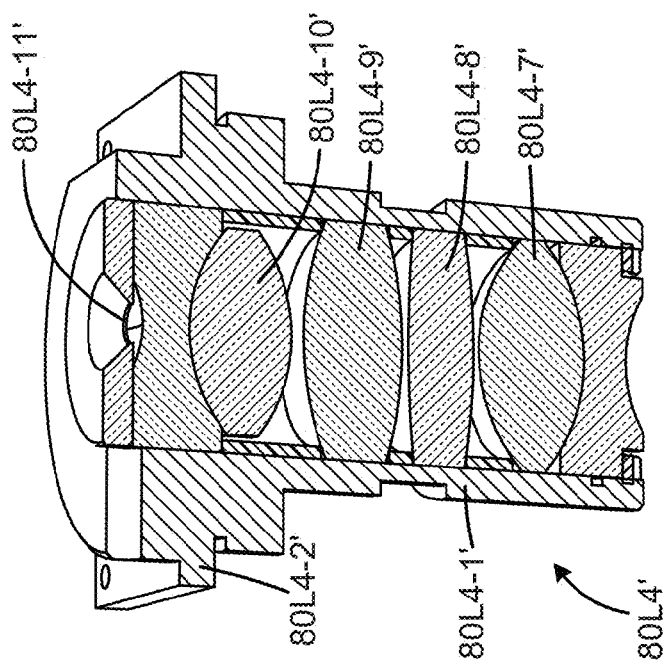
FIG. 7B is a cross-sectional view of the assembly of FIG. 7A.

The camera tube assembly 80L4' is further illustrated in FIGS. 7A and 7B. The outer tube housing 80L4-1' is fabricated of an electrically conductive, non-ferrous material, such as brass or aluminum. The length of the tube plus the length of the beam splitter block is at least three times the inner diameter of the tube, to provide shielding of RF energy from leaking from the camera and into the MRI magnet room. Lenses 80L4-7'-80L4-10' provide an optical path from the camera to the field stop 80L4-11'.

The focus barrels 70L3' and 80L3' may be fabricated of a plastic material, since these elements are fitted outside the focus tubes and the display/camera tube housings.

FIGS. 6A-6B illustrate an exemplary embodiment of an eyepiece 110L' of the system 50'. The right eyepiece is identical to the left eyepiece. An eyepiece block 110L1A' defines a receptacle 110L1H' for the eyepiece optics 110L1D'. Eyepiece covers 110L1B' and 110L1C' are assembled to the block. These elements can be fabricated of plastic material, as they may extend into the head coil. Alternatively, the block and cover elements may be fabricated of a non-ferrous material such as brass or aluminum. Four fiber optic bundles are mounted between the respective LEDs 110L1J' of LED assembly 110L1I' and holes 110L1K' formed in the eyepiece retainer 110L1F' at radial positions at 90 degree spacing, and are preferably mounted so as to direct IR energy at the center of the observer's eye. It is preferable to illuminate the eye with IR energy as much as possible with the IR emitters, to obtain a good IR image of the eye to improve the tracking of the eye. The LEDs are selected to generate IR radiation, and are preferably non-ferrous. With the ends of the fiber optic bundles serving as IR emitters, the patient's eye will be illuminated with IR energy. In this exemplary embodiment, the optics 110L1D' has three lenses 110L1G1. If the LEDs are totally non-ferrous, they may be mounted close to the eyepiece retainer, and eliminate the need for the fiber optic bundles. Alternatively the LEDs could be located in other locations, e.g. close to the camera, and the optical fiber bundles lengthened as needed. The fiber bundles may even be located at least through part of their length outside the housing, as the IR light typically does not affect the MRI image quality.

Figure 8A:
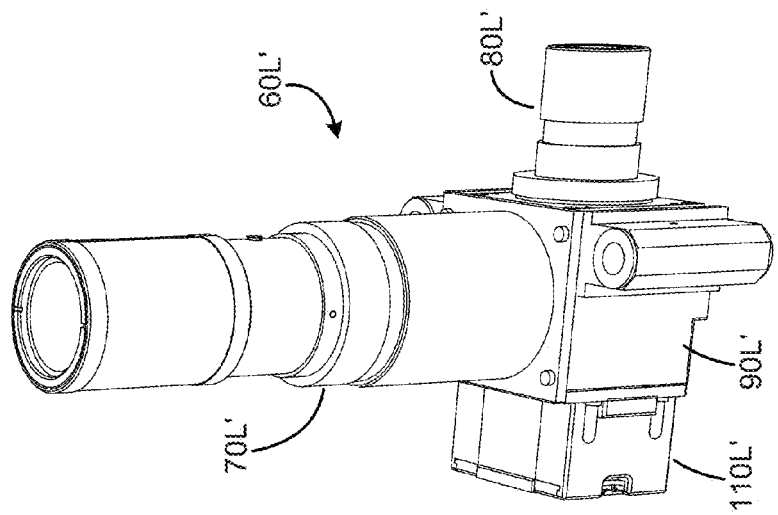
FIG. 8A is an isometric view of a camera, eyepiece and display assembly for one eye, of the system of FIG. 2, with an outer tube housing of the display tube removed.
Figure 8B:
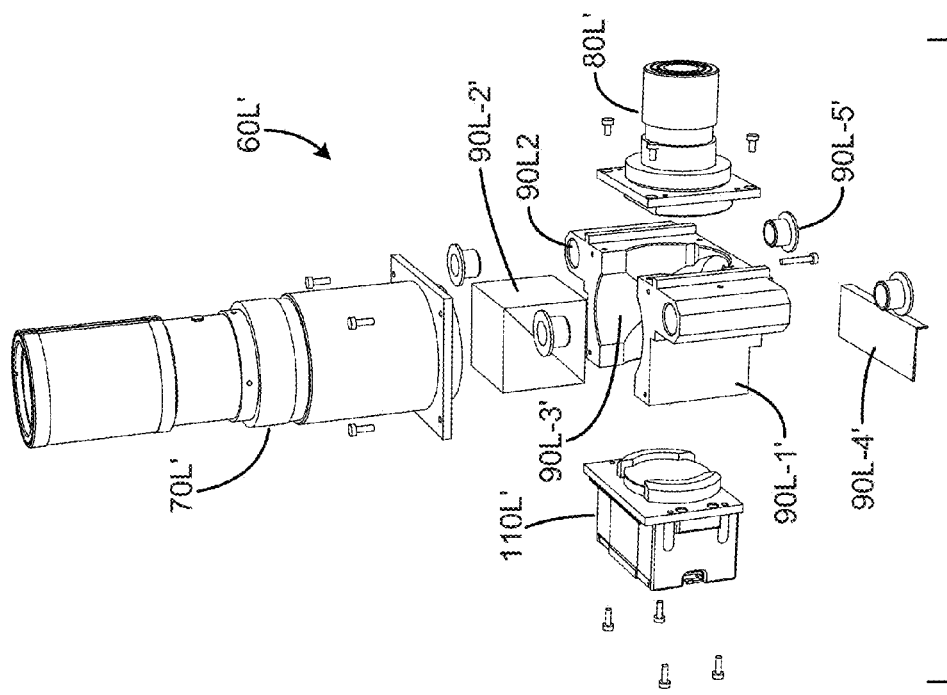
FIG. 8B is a partially exploded view of the assembly of FIG. 8A.
Figure 9A:
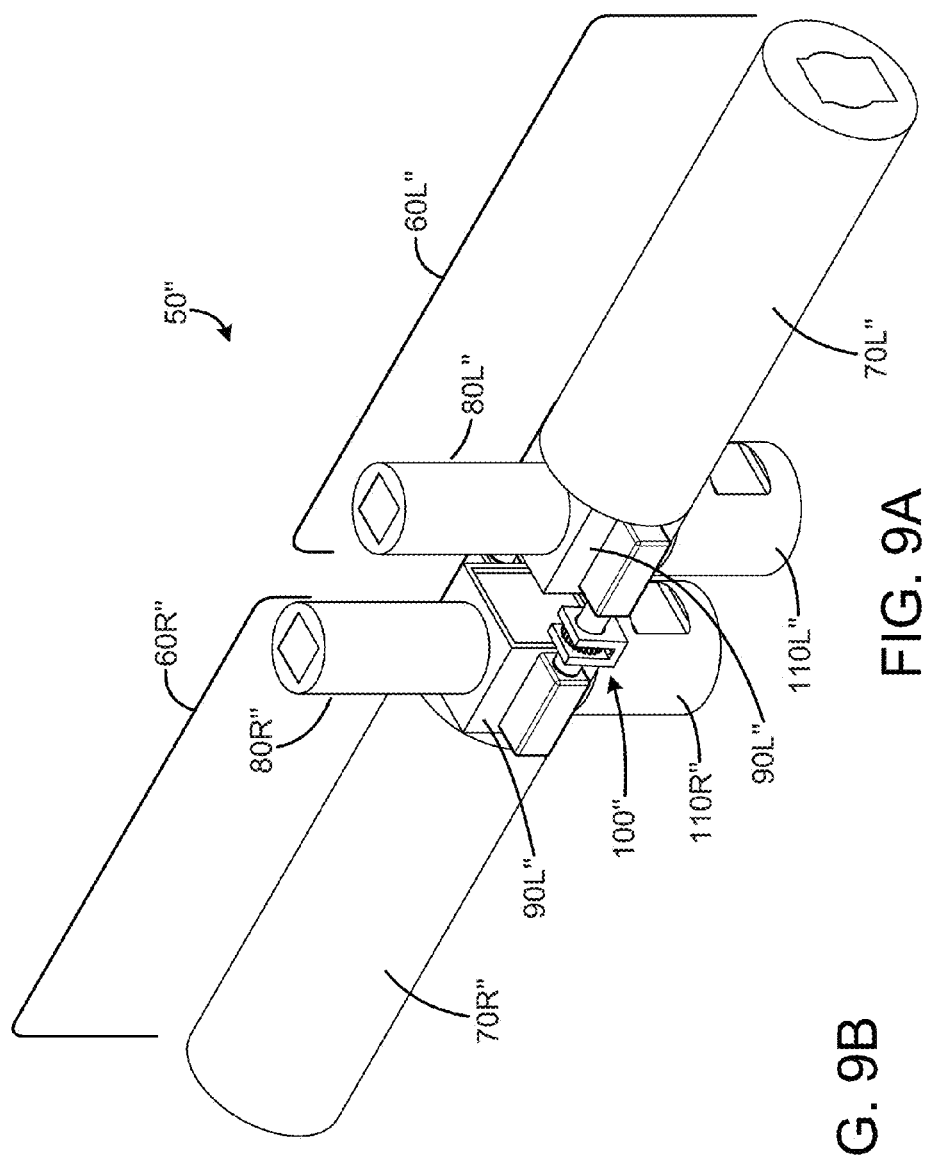
FIGS. 9A-9C illustrate another exemplary embodiment of a heads-up display and eye-tracker system, with FIG. 9C illustrating exemplary optics for the system.
Figure 9B:
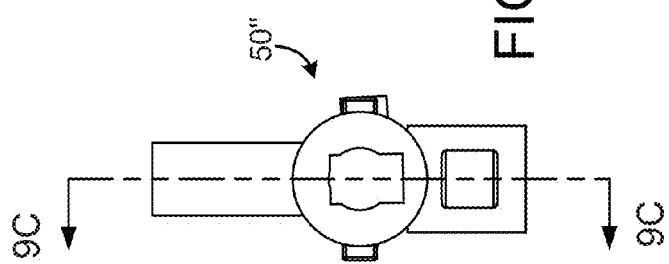
Figure 9C:
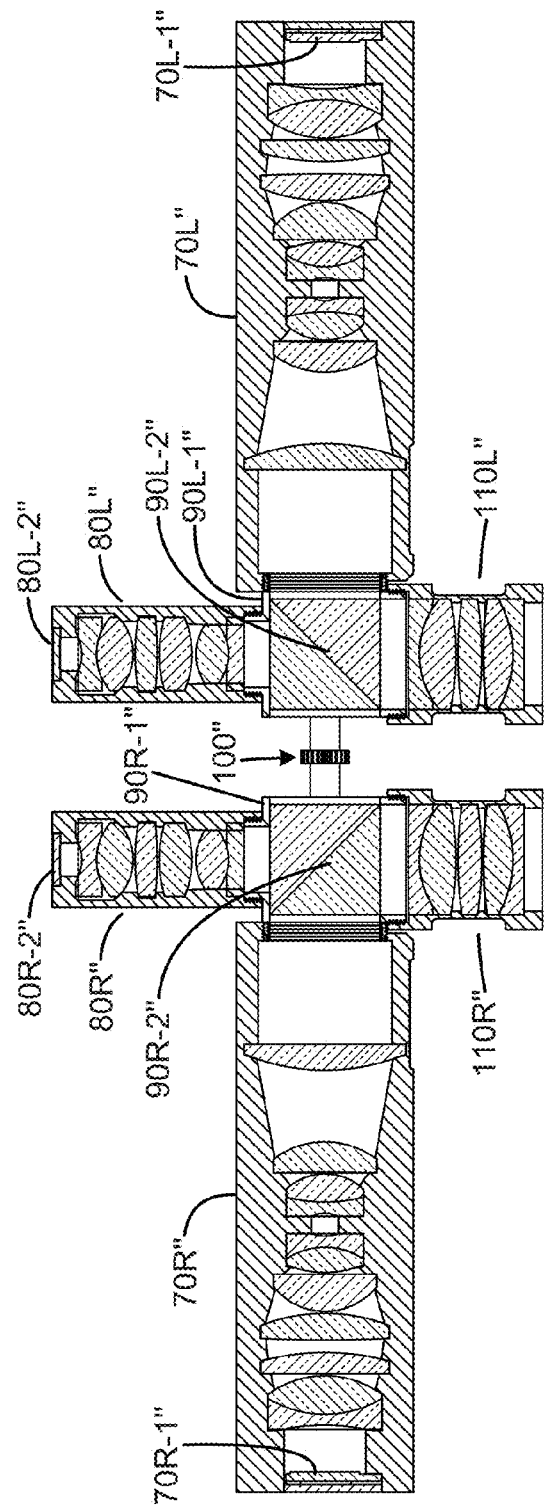

The eyepiece 110L' is assembled to the beam splitter block 90L1, as illustrated in FIGS. 8A and 8B, showing the assembly 60L'. As shown therein, the beam splitter cube 90L-2' is fitted into a receptacle (90L-3') defined by the beam splitter block 90L-1'. Each of the assemblies 70:', 80L' and 110L' is secured to a corresponding side face of the block 90L-1' by brass threaded fasteners or other attachment means. The remaining open side face of the block is closed by cover 90L-4', fabricated of an electrically conductive, non-ferrous material. Also shown in FIG. 8B are shaft bushings 90L-5' which fit into the shaft sleeves 90L2 in the block 90L-1'

FIGS. 9A-16C illustrate features of a further embodiment of a heads-up display and eye-tracker system 50". The elements corresponding to the elements of system 50 (FIGS. 1, 1A) or 50' (FIGS. 2-8B) are identified with the same number and a double prime, e.g. 60R" corresponding to element 60 of FIGS. 1 and 1A. Thus, the system 50" includes left and right eye assemblies 60L" and 60R" connected together by mechanism 100". The assemblies include left and right display assemblies 70L", 70R", left and right camera assemblies 80L" and 80R", left and right eyepiece assemblies 110L" and 110R", and left and right beam splitter assemblies 100L" and 100R", assembled to beam splitter blocks 90L-1" and 90R-1", respectively. Cameras 80L-2" and 80R-2" are fitted into the camera tubes, and displays 70L-1" and 70R-1" are fitted into the display tubes, as with the embodiments described above regarding FIGS. 1-8B. Beam splitter cubes 90L-2" and 90R-2" are fitted into beam splitter blocks 90L-1" and 90R-1". The optics for the display and camera paths are illustrated as well.

FIG. 10 shows elements of the mechanism 100", including an IPD belt 102I" and IPD gear 102N" for adjusting for the IPD of the patient, by adjusting the distance between assemblies 60L" and 60R".

Figure 11:
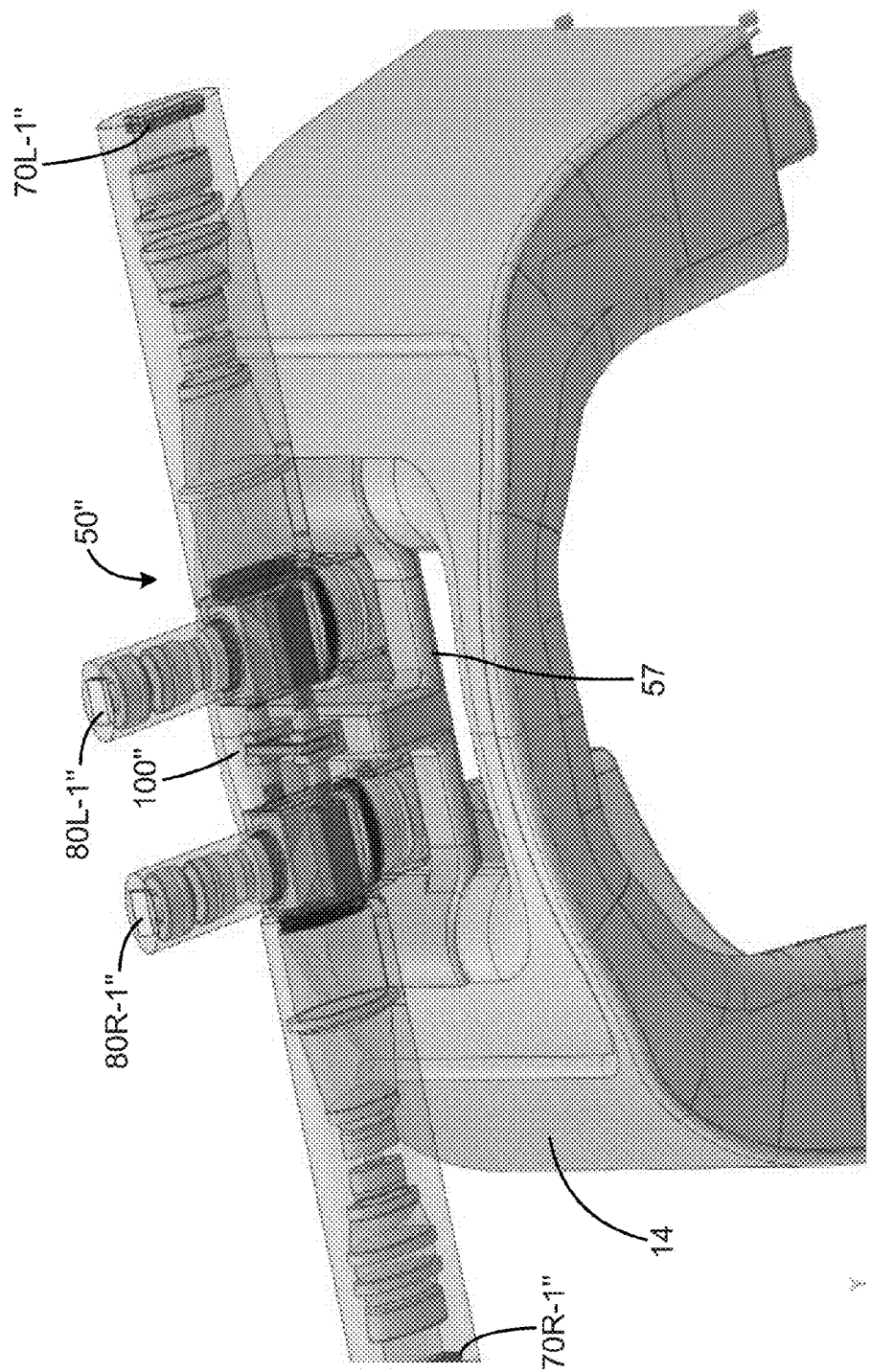
FIGS. 11 and 12 show the system of FIGS. 9A-9C in place on an MRI head coil.
Figure 12:
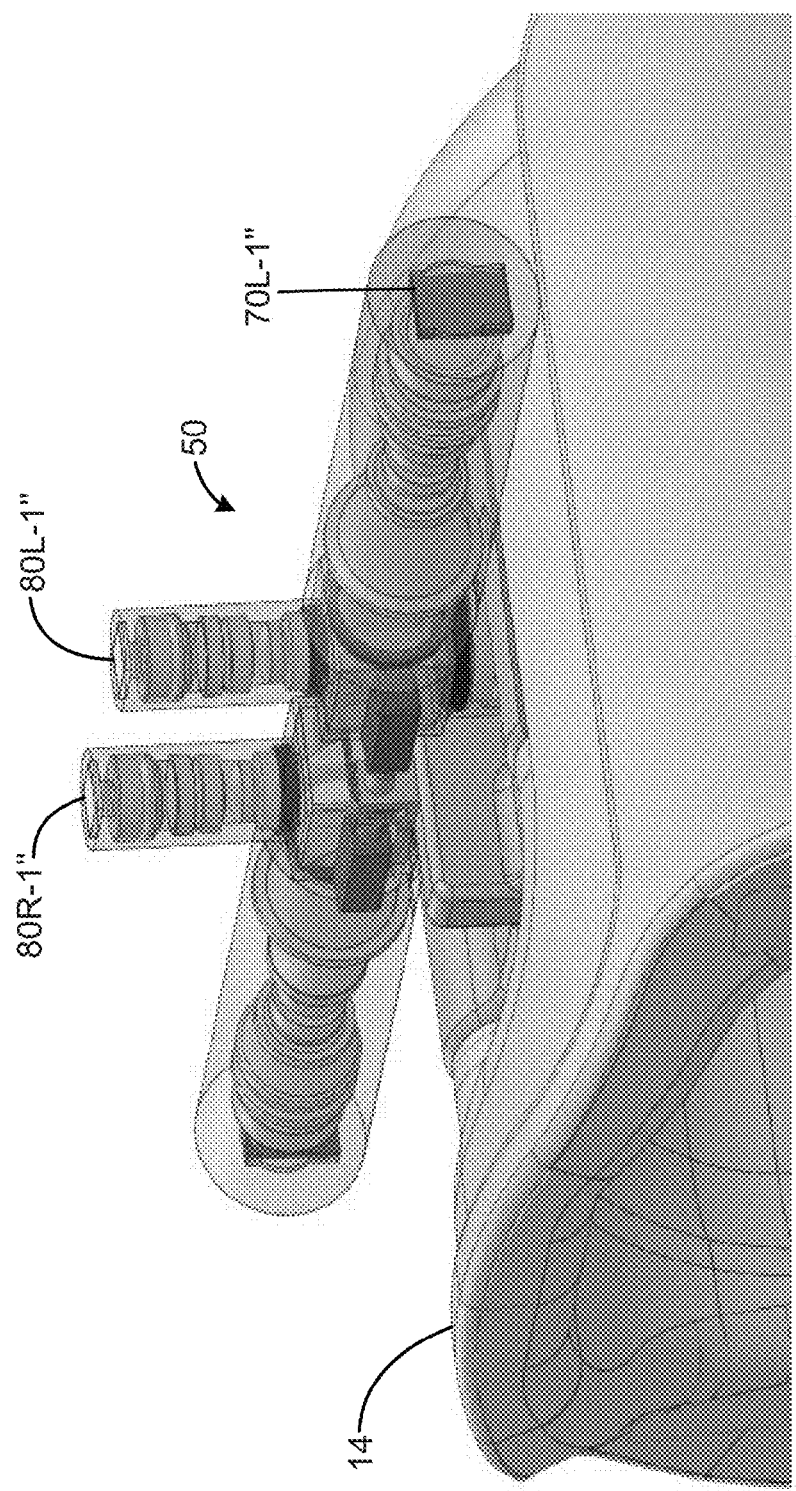

FIGS. 11-12 show the system 50" positioned on a head coil, with base 57 of the system supporting the system over the head coil opening. The base can be modified to accommodate the head coils of different MRI manufacturers.

Figure 13:
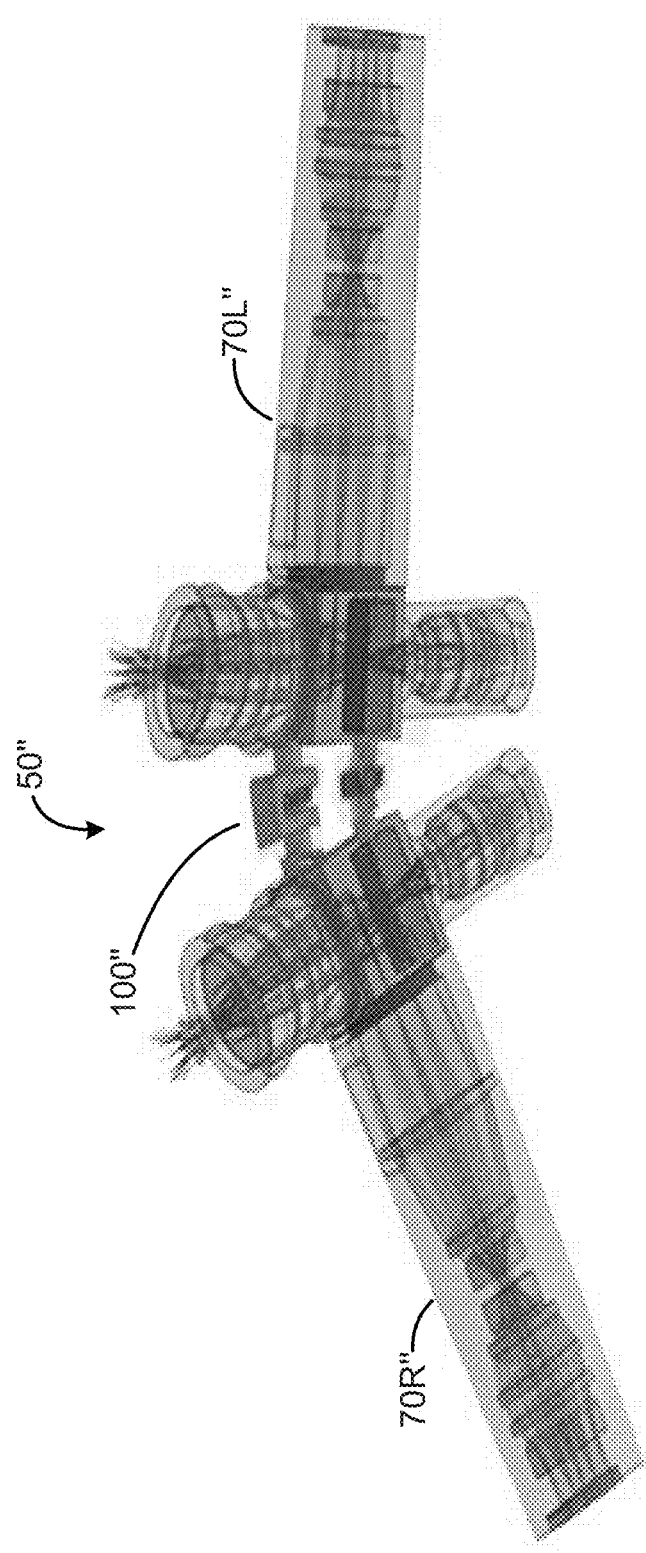
FIG. 13 illustrates the eye pieces of the system of FIGS. 9A-9C being tilted to an angular offset to change the field of view.
Figure 14:
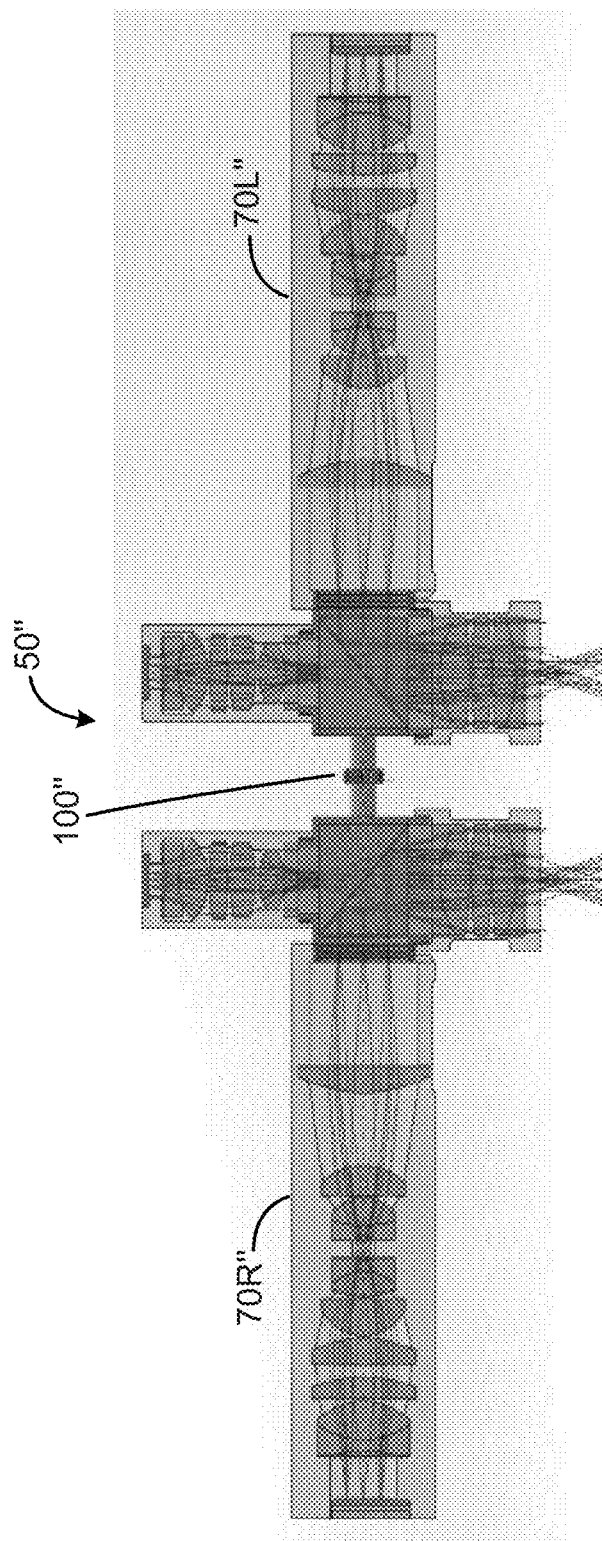
FIG. 14 shows the system of FIGS. 9A-9C, with the eye-pieces in parallel arrangement.
Figure 16C:
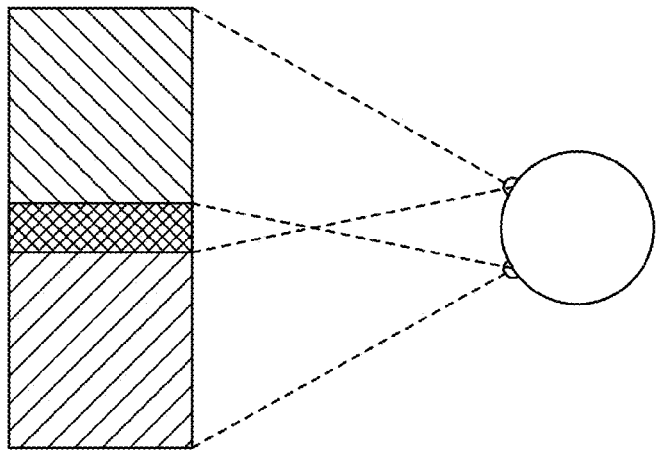
FIGS. 16A, 16B, 16C show different fields of view of the system of FIGS. 9A-9C.
Figure 16B:
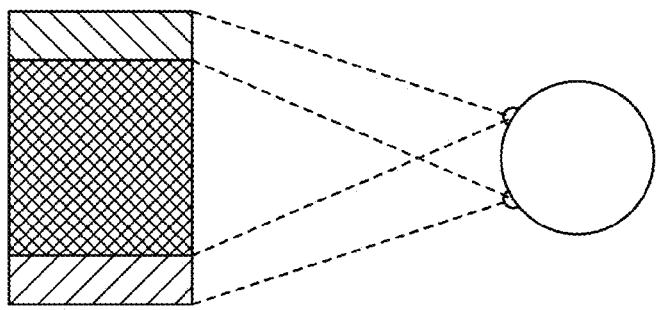
Figure 16A:
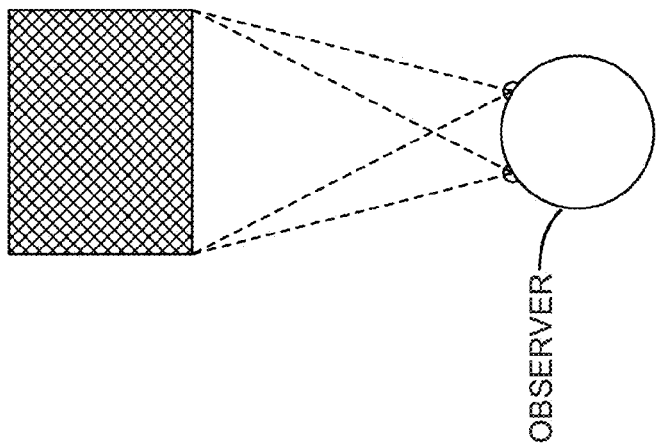

FIGS. 13 and 14 illustrate field of view adjustment features of the system 50", as well as light rays through the display and camera optics, wherein the adjustment mechanism 100" allows for adjustment of the angular orientation of the left and right display assemblies 70L" and 70R". FIG. 14 shows the case in which the display assemblies 70L" and 70R" are aligned along a linear axis, i.e. at zero degree tilt. In this case, the observer will have 50 degree FOV, in an exemplary embodiment. This means there will be 100 percent overlap for both displays, as illustrated in FIG. 16A. Now consider the system configuration shown in FIG. 13, in which the displays are oriented by mechanism 100" with a 20 degree tilt from the linear case (FIG. 14). This will increase the FOV to about 80 degrees, with only a 20 percent overlap between the images (FIG. 16C). FIG. 16B shows an intermediate case, with 80 percent overlap of the images, with a 58.5 degree FOV.

A further embodiment is illustrated in FIG. 17. The system 50''' is a display system, similar to that illustrated in FIG. 2, but without the eye tracker camera and related optics elements. Instead, the side of the beam splitters 90L" and 90R" facing away from the patient's eyes is closed by a non-ferrous, electrically conductive plate, e.g. an aluminum or brass plate, with an interior surface facing the beam splitter which is non-reflective of light. The interior surface may be painted black for example. The system 50" may be employed in the MRI tube to present display images to the patient during MRI procedures.

Although the foregoing has been a description and illustration of specific embodiments of the subject matter, various modifications and changes thereto can be made by persons skilled in the art without departing from the scope and spirit of the invention. Further, while the foregoing embodiments illustrate binocular systems, monocular systems may also be employed utilizing the left eye or the right eye system, individually.

What is claimed is:

1. A display system for use with a patient in an MRI tube during an MRI procedure, comprising:
    an electronic display assembly including an outer display tube housing for housing an electronic display device for generating images, the outer display tube housing fabricated of an electrically conductive, non-ferrous material;
    an eyepiece assembly including an outer housing;

a beam splitter assembly comprising a beam splitter block having a receptacle holding a beam splitter, the block formed of an electrically conductive, non-ferrous material;

the outer display tube of the display assembly configured to mount to a first side of the beam splitter block, the first side having an opening providing a first optical path from the electronic display device to the beam splitter;

the eyepiece assembly configured to mount to a second side of the beam splitter block, the second side having an opening providing a second optical path to the beam splitter;

an RF shielding system configured to block RF energy emitted by the electronic display device and cause interference to the MRI signals, thereby shielding the display assembly from affecting the MRI images, said shielding system comprising the outer display tube housing, the outer display tube housing having a sufficient length in relation to an inner dimension of the housing so that the outer display tube housing and the beam splitter block effectively prevent display radiation emitted by the electronic display device from affecting the MRI images, and wherein the shielding system is free of a conductive mesh in the first optical path, thereby avoiding the degradation caused by a conductive mesh in the optical path;

the beam splitter assembly configured to reflect image light from the display device through the eyepiece assembly to one of the patient's eyes.

2. The system of claim 1, wherein the electronic display device comprises a high definition display device having at least a nominal display resolution of 1920 by 1200 pixels, and wherein the display tube length is at least three times an inner width dimension to form a waveguide to block RF energy emitted by the display device from passing out of the display system to affect the MRI imaging.

3. The system of claim 1, wherein the electronic display device is mounted within the outer display tube housing at a distal end of the tube housing away from the beam splitter assembly, the system further comprising:

a display tube cover attached to the distal end of the display tube housing, and fabricated of electrically conductive, non-ferrous material.

4. The system of claim 1, wherein the electronic display device is an organic light emitting diode (OLED) display device having a nominal resolution of 1920 by 1200 pixels.

5. The system of claim 1, wherein the patient is positioned within the tube with the patient's head within an MRI head coil, and wherein the eyepiece assembly is configured to be supported by the head coil above the patient's eye.

6. The system of claim 1, further comprising display optical lenses disposed between the electronic display and the beam splitter within the outer display housing tube, and wherein a field stop is defined within the outer display housing tube, and through which all visible light rays from the display device pass.

7. A display system for use with a patient in an MRI tube, comprising:

left and right electronic display assemblies for the patient's left and right eyes, each display assembly including an electronic display device, an outer display tube housing for housing the electronic display device for generating images, and display optical lenses;

left and right eyepiece assemblies, each assembly including an outer housing;

left and right beam splitter assemblies, each comprising a beam splitter block having a receptacle holding a beam splitter, the block formed of an electrically conductive, non-ferrous material;

the left and right display assemblies respectively configured to mount to a first side of the left and right beam splitter blocks, the first side having an opening providing a first optical path to the respective beam splitter;

the left and right eyepiece assemblies respectively configured to mount to a second side of the left and right beam splitter blocks, the second side having an opening providing a second optical path to the beam splitter;

the left and right beam splitter assemblies configured to respectively reflect image light from the respective display devices through the respective left and right eyepiece assembly to the patient's eyes;

wherein the respective left and right electronic display assemblies are mounted at a distal end of the respective outer display tube housings, and the display optical lenses are mounted within the respective outer display tube housings; and an RF shielding system configured to block RF energy emitted by the electronic display devices and prevent interference to the MRI signals, the shielding system free of electrically conductive mesh situated in the optical paths between the respective electronic display devices and the patient's eyes.

8. The system of claim 7, wherein said RF shielding system comprises each of said display tube housings, wherein said display tube housings are fabricated of an electrically conductive, non-ferrous material, and each of said display tube housings has a display tube length dimension and an internal diameter dimension, the beam splitter block has a block length dimension, and wherein the sum of the display tube length dimension and the block length dimension is at least three times the internal diameter dimension to block RF energy from passing out of the system to affect the MRI imaging.

9. The system of claim 7, wherein each display assembly includes a field stop defined within the outer display housing tube, through which all visible light rays from the display device pass.

10. The system of claim 7, wherein the electronic display device is a high resolution display device having a nominal resolution of at least 1920 by 1200 pixels.

11. The system of claim 7, wherein the patient is positioned within the MRI tube with the patient's head within an MRI head coil, and wherein the system is configured to be supported by the head coil with the eyepiece assemblies above the patient's eyes.

12. The system of claim 7, further comprising:

an adjustment mechanism for providing adjustment of an angular orientation of the left and right display assemblies, to provide a variable field of view of the system.

13. A head-up display and eye-tracker system for use with a patient in an MRI tube during an MRI procedure, comprising:

an electronic display assembly including an outer display tube housing for housing an electronic display device for generating images;

an eye-tracker camera assembly including an outer camera tube housing for housing an electronic camera sensor;

an eyepiece assembly including an outer housing;

a beam splitter assembly comprising a beam splitter block having a receptacle holding a beam splitter, the block formed of an electrically conductive, non-ferrous material;

the display assembly configured to mount to a first side of the beam splitter block, the first side having an opening providing a first optical path to the beam splitter;

the camera assembly configured to mount to a second side of the beam splitter block, the second side having an opening providing a second optical path to the beam splitter;

the eyepiece assembly respectively configured to mount to a third side of the beam splitter block, the third side having an opening providing a third optical path to the beam splitter;

the beam splitter assembly configured to reflect image light from the display device through the eyepiece assembly to one of the patient's eyes, and to allow light reflected from the patient's eye to pass through the beam splitter to the camera sensor to capture images of the patient's eye; and an RF shielding system configured to block RF energy emitted by the electronic display device and the electronic camera sensor and prevent interference to the MRI signals, the shielding system free of electrically conductive mesh situated in the optical paths between the respective electronic display devices and the patient's eyes.

14. The system of claim 13, further comprising:
an infrared emitter system configured to illuminate the patient's eye with infrared energy;
a filter mounted in an optical path to the camera to block visible light energy and allow infrared energy to pass to the camera sensor.

15. The system of claim 14, wherein the infrared emitter system comprises an emitter set assembled to the eyepiece assembly.

16. The system of claim 13, wherein said RF shielding system comprises said display tube housing, said display tube housing fabricated of an electrically conductive, non-ferrous material, said display tube housing having a display tube length dimension and an internal diameter dimension, the beam splitter block has a block length dimension, and wherein the sum of the display tube length dimension and the block length dimension is at least three times the internal diameter dimension to block RF energy from passing out of the electronic display device to affect the MRI imaging.

17. The system of claim 16, further comprising:
a display tube cover attached to an end of the display tube housing distal from the beam splitter block, and fabricated of electrically conductive, non-ferrous material; and
a camera tube cover attached to an end of the camera tube housing distal from the beam splitter block, and fabricated of electrically conductive, non-ferrous material.

18. The system of claim 13, wherein said RF shielding system comprises said camera tube housing, said camera tube housing fabricated of an electrically conductive, non-ferrous material.

19. The system of claim 13, wherein the electronic display device is a high resolution display device having a nominal resolution of at least 1920 by 1200 pixels.

20. The system of claim 13, wherein the patient is positioned within the tube with the patient's head within an MRI head coil, and wherein the system is configured to be supported by the head coil above the patient's eye, so that the eye-tracker sensor has an unobstructed view of the patient's eye.

21. The system of claim 13, further comprising an adjustment mechanism for providing adjustment of an angular orientation of the left and right display assemblies, to provide a variable field of view of the system.

22. The system of claim 13, further comprising a focus mechanism configured to move the camera sensor through a range of movement toward and away from the beam splitter block.

23. A head-up display and eye-tracker system for use with a patient in an MRI tube, comprising:
left and right electronic display assemblies for the patient's left and right eyes, each display assembly including an outer display tube housing for housing an electronic display device for generating images, each outer tube housing being fabricated of an electrically conductive, non-ferrous material;
left and right eye-tracker camera assemblies, each camera assembly including an outer camera tube housing for housing an electronic camera sensor, the outer tube camera housing being fabricated of an electrically conductive, non-ferrous material;
left and right eyepiece assemblies, each assembly including an outer housing;
left and right beam splitter assemblies, each comprising a beam splitter block having a receptacle holding a beam splitter, the block formed of an electrically conductive, non-ferrous material;
the left and right display assemblies respectively configured to mount to a first side of the left and right beam splitter blocks, the first side having an opening providing a first optical path to the respective beam splitter;
the left and right camera assemblies respectively configured to mount to a second side of the left and right beam splitter blocks, the second side having an opening providing a second optical path to the respective beam splitter;
the left and right eyepiece assemblies respectively configured to mount to a third side of the left and right beam splitter blocks, the third side having an opening providing a third optical path to the beam splitter;
the left and right beam splitter assemblies configured to respectively reflect image light from the respective display devices through the respective left and right eyepiece assembly to the patient's eyes, and to allow light reflected from the patient's eyes to pass through the beam splitter to the respective first and second camera sensor to capture respective images of the patient's left and right eyes; and
an RF shielding system configured to block RF energy emitted by the electronic display device and the electronic camera sensor and prevent interference to the MRI signals, the shielding system free of electrically conductive mesh situated in the optical paths between the respective electronic display devices and the patient's eyes, the RF shielding system comprising the outer display tube housings, the outer tube camera housings and the beam splitter blocks.

24. The system of claim 23, further comprising:
infrared emitters configured to illuminate the respective eye with infrared energy;
respective first and second filters mounted in the optical path to the first and second cameras to block visible light energy and allow infrared energy to pass to the first and second camera sensors.

25. The system of claim 24, wherein the infrared emitters comprise a left emitter set assembled to the left eyepiece assembly and a right emitter set assembled to the right eyepiece assembly.

26. The system of claim 23, wherein each of said display tube housings has a display tube length dimension and an internal diameter dimension, the beam splitter block has a block length dimension, and wherein the sum of the display tube length dimension and the block length dimension is at least three times the internal diameter dimension to block RF energy from passing out of the system to affect the MRI imaging.

27. The system of claim 23, further comprising a mechanism configured to connect the respective left and right beam splitter blocks and to adjust for the patient's inter-pupil distance (IPD).

28. The system of claim 23, wherein the first optical path is orthogonal to the second and third optical paths.

29. The system of claim 23, further comprising:
first and second display tube covers attached to respective ends of the first and second display tube housings distal from the beam splitter block, and fabricated of electrically conductive, non-ferrous material; and
first and second camera tube covers attached to respective ends of the first and second camera tube housings distal from the beam splitter block, and fabricated of electrically conductive, non-ferrous material.

30. The system of claim 23, wherein the patient is positioned within the MRI tube with the patient's head within an MRI head coil, and wherein the system is configured to be supported by the head coil above the patient's eye, so that the eye-tracker sensors have an unobstructed view of the patient's eyes.

31. The system of claim 23, further comprising:
an adjustment mechanism for providing adjustment of an angular orientation of the left and right display assemblies, to provide a variable field of view of the system.

32. A head-up display and eye-tracker system for use in an MRI room, comprising:
left and right electronic display assemblies for the observer's left and right eyes, each display assembly including an outer display tube housing for housing an electronic display device and a display lens set, the outer display tube housing being fabricated of an electrically conductive, non-ferrous material;
left and right eye-tracker camera assemblies, each camera assembly including an outer camera tube housing for housing an electronic camera sensor and a camera lens set, the outer camera tube housing being fabricated of an electrically conductive, non-ferrous material and having an inner diameter and a length dimension;
left and right eyepiece assemblies, each assembly including an outer eyepiece housing for housing eyepiece optics comprising an eyepiece lens set;
left and right beam splitter assemblies, each comprising a beam splitter block having a receptacle for holding a beam splitter, the block formed of an electrically conductive, non-ferrous material;
the left and right display assemblies respectively configured to mount to a first side of the left and right beam splitter blocks, the first side having an opening providing an optical path to the respective beam splitter;
the left and right camera assemblies respectively configured to mount to a second side of the left and right beam splitter blocks, the first side and second side orthogonal to each other, the second side having an opening providing an optical path to the respective beam splitter;
the left and right eyepiece assemblies respectively configured to mount to a third side of the left and right beam splitter blocks, the third side opposite and parallel to the second side, the third side having an opening providing an optical path to the beam splitter;
the left and right beam splitter assemblies configured to respectively reflect image light through the respective left and right eyepiece optics to the patient's eyes, and to allow light from the patient's eyes to pass through the beam splitter to the respective first and second camera sensors to provide an image of the patient's eyes; and
an RF shield system free of conductive mesh interposed between the respective display devices and the patient's eyes, the RF shield system configured to block energy emitted by the display devices and camera sensors from affecting MRI imaging procedures, the system comprising the electrically conductive outer display tubes, the outer camera tubes and the beam splitter blocks.

33. The system of claim 32, further comprising:
infrared emitters mounted in each eyepiece to illuminate the respective eye with infrared energy;
respective first and second filters mounted in the optical path to the first and second cameras to block visible light energy and allow only infrared energy to pass to the first and second camera sensors.

34. The system of claim 32, wherein each of said display tube housings has a display length dimension and an internal diameter dimension, and wherein the display length dimension is at least three times the internal diameter dimension to block RF energy from passing out of the system to affect the MRI imaging.

* * * * *